US009384906B2

(12) United States Patent
Abe et al.

(10) Patent No.: US 9,384,906 B2
(45) Date of Patent: Jul. 5, 2016

(54) NON-AQUEOUS ELECTROLYTE SOLUTION AND ELECTRICITY-STORAGE DEVICE USING SAME

(75) Inventors: Koji Abe, Yamaguchi (JP); Kei Shimamoto, Yamaguchi (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 218 days.

(21) Appl. No.: 14/111,015

(22) PCT Filed: Apr. 12, 2012

(86) PCT No.: PCT/JP2012/060073
§ 371 (c)(1),
(2), (4) Date: Oct. 10, 2013

(87) PCT Pub. No.: WO2012/141270
PCT Pub. Date: Oct. 18, 2012

(65) Prior Publication Data
US 2014/0030610 A1  Jan. 30, 2014

(30) Foreign Application Priority Data

| Apr. 12, 2011 | (JP) | 2011-088035 |
| Jul. 8, 2011 | (JP) | 2011-151848 |
| Oct. 14, 2011 | (JP) | 2011-227319 |

(51) Int. Cl.
*H01M 10/0567* (2010.01)
*H01G 11/54* (2013.01)
*H01G 11/58* (2013.01)
*H01M 10/0525* (2010.01)
*H01M 10/056* (2010.01)
*H01G 11/64* (2013.01)
*C07F 9/53* (2006.01)
*C07F 9/6571* (2006.01)
*C07F 9/32* (2006.01)
*C07F 9/40* (2006.01)
*H01M 10/0569* (2010.01)
*H01G 11/60* (2013.01)
*H01M 10/0568* (2010.01)

(52) U.S. Cl.
CPC ............. *H01G 11/54* (2013.01); *C07F 9/3211* (2013.01); *C07F 9/4006* (2013.01); *C07F 9/5304* (2013.01); *C07F 9/657181* (2013.01); *H01G 11/58* (2013.01); *H01G 11/64* (2013.01); *H01M 10/056* (2013.01); *H01M 10/0525* (2013.01); *H01M 10/0567* (2013.01); *H01G 11/60* (2013.01); *H01M 10/0568* (2013.01); *H01M 10/0569* (2013.01); *Y02E 60/122* (2013.01); *Y02E 60/13* (2013.01)

(58) Field of Classification Search
CPC .................. H01M 10/052; H01M 10/0567
See application file for complete search history.

(56) References Cited

U.S. PATENT DOCUMENTS

| 3,943,200 | A | 3/1976 | Honig et al. |
| 5,273,549 | A | 12/1993 | Didier et al. |
| 2006/0246356 | A1 | 11/2006 | Abe et al. |
| 2009/0281205 | A1 | 11/2009 | Piotrowski et al. |
| 2010/0035147 | A1* | 2/2010 | Kotato ............... H01M 10/052 429/203 |
| 2011/0052980 | A1 | 3/2011 | Sakata et al. |

FOREIGN PATENT DOCUMENTS

| CN | 101083345 A | 12/2007 |
| CN | 101440105 A | 5/2009 |

(Continued)

OTHER PUBLICATIONS

The Extended European Search Report issued Sep. 10, 2014, in European Patent Application No. 12771624.9
(Continued)

*Primary Examiner* — Stewart Fraser
*Assistant Examiner* — Olatunji Godo
(74) *Attorney, Agent, or Firm* — Oblon, McClelland, Maier & Neustadt, L.L.P.

(57) ABSTRACT

The present invention provides a nonaqueous electrolytic solution capable of improving electrochemical characteristics at high temperatures, which comprises at least one organic phosphorus compound represented by the following general formula (I), an energy storage device using the nonaqueous electrolytic solution, and a specific organic phosphorus compound.

$$\left[ \begin{matrix} R^1 \\ R^2 \end{matrix} \!\!\! \diagdown \!\! \underset{\underset{}{}}{\overset{\overset{O}{\|}}{P}} \!\!-\!\! \left( \underset{\underset{R^4}{|}}{\overset{\overset{R^3}{|}}{C}} \right)_{\!\!m} \!\!\!\!-\!\! (O)n \!-\! \overset{\overset{O}{\|}}{C} \!\!-\!\! X \right]_q \qquad (I)$$

(In the formula, $R^1$ and $R^2$ each independently represent an alkyl group, a cycloalkyl group, an alkenyl group, an alkynyl group, an alkoxy group, a cycloalkoxy group, an alkenyloxy group, an alkynyloxy group, a halogenoalkyl group, a halogenoalkoxy group, an aryl group, or an aryloxy group; $R^3$ and $R^4$ each independently represent a hydrogen atom, a halogen atom, or an alkyl group; m is an integer of from 1 to 4, n is 0 or 1, q is 1 or 2. When q is 1 and n is 0, X represents an alkoxy group, an alkynyloxy group, an alkyloxyalkoxy group, an aryloxy group, etc.; when q is 1 and n is 1, X represents an alkyl group, an alkynyl group, an alkoxy group, an alkynyloxy group, an alkyloxyalkoxy group, etc.; and when q is 2, X represents —O-$L^3$-O—, —OC(=O)—C(=O)O—, or a single bond.)

20 Claims, No Drawings

(56) References Cited

FOREIGN PATENT DOCUMENTS

| | | |
|---|---|---|
| CN | 101938008 A | 1/2011 |
| CN | 101948484 A | 1/2011 |
| DE | 2 152 876 | 4/1973 |
| JP | 6-100575 A | 4/1994 |
| JP | 10-189039 A | 7/1998 |
| JP | 2003-229173 A | 8/2003 |
| JP | 2009-70615 A | 4/2009 |
| JP | 2010-192457 A | 9/2010 |
| WO | WO 2007/001717 A2 | 1/2007 |
| WO | WO 2008/123038 A1 | 10/2008 |

OTHER PUBLICATIONS

International Search Report issued Jul. 24, 2012, in PCT/JP2012/060073.

Christopher D. Smith, et al., "[3+2] Cycloaddition of acetylenes with azides to give 1,4-disubstituted 1,2,3-triazoles in a modular flow reactor", Organic & Biomoleculer Chemistry, vol. 5, Apr. 16, 2007, pp. 1559-1561.

Antje Teichert, et al., "One-Pot Homolytic Aromatic Substitutions/HWE Olefinations under Microwave Conditions for the Formation of a Small Oxindole Library", Organic Letters, vol. 6, No. 20, 2004, pp. 3477-3480.

* cited by examiner

NON-AQUEOUS ELECTROLYTE SOLUTION AND ELECTRICITY-STORAGE DEVICE USING SAME

TECHNICAL FIELD

The present invention relates to a nonaqueous electrolytic solution capable of improving electrochemical characteristics at high temperatures, an energy storage device using it, and a specific organic phosphorus compound.

BACKGROUND ART

In recent years, energy storage devices, especially lithium secondary batteries have been widely used as power supplies for electronic devices, such as mobile telephones, notebook-size personal computers and the like, power supplies for electric vehicles, as well as for electric power storage, etc. The batteries mounted on these electronic devices and vehicles may be used at midsummer high temperatures or in the environments warmed through heat generation by those electronic devices.

A lithium secondary battery, a type of energy storage device is mainly constituted of a positive electrode and a negative electrode containing a material capable of absorbing and releasing lithium, and a nonaqueous electrolytic solution containing a lithium salt and a non-aqueous solvent. For the non-aqueous solvent, used are carbonates, such as ethylene carbonate (EC), propylene carbonate (PC), etc.

As the negative electrode of the lithium secondary battery, known are metal lithium, and metal compounds (metal elemental substances, oxides, alloys with lithium, etc.) and carbon materials capable of absorbing and releasing lithium. In particular, a lithium secondary battery using a nonaqueous electrolytic solution and using a carbon material capable of absorbing and releasing lithium, such as coke, graphite (artificial graphite, natural graphite) or the like, has been widely put into practical use. The above-mentioned negative electrode material stores and releases lithium and electron at an extremely electronegative potential equivalent to that for lithium metal, and therefore especially at high temperatures, there is a possibility that many solvents would be reductively decomposed by the negative electrode material of the type; and consequently, the solvent in the electrolytic solution would be partly reductively decomposed on the negative electrode irrespective of the type of the negative electrode material, and as a result, there occurs a problem in that lithium ion movement is thereby retarded owing to deposition of decomposed products and gas generation and the battery characteristics, such as cycle properties and the like especially at high temperatures are thereby worsened. Further, it is known that a lithium secondary battery using a lithium metal or its alloy, or a metal elemental substance, such as tin, silicon or the like or its metal oxide as the negative electrode material therein may have a high initial battery capacity but the battery capacity and the battery performance thereof, such as cycle properties greatly worsens, since the micronized powdering of the material is promoted during cycles thereby bringing about accelerated reductive decomposition of the non-aqueous solvent, as compared with the negative electrode of a carbon material.

On the other hand, a material capable of absorbing and releasing lithium, such as $LiCoO_2$, $LiMn_2O_4$, $LiNiO_2$ and $LiFePO_4$ that are used as a positive electrode material stores and releases lithium and electron at a lithium-based electropositive voltage of not lower than 3.5 V, and therefore especially at high temperatures, there is a possibility that many solvents would be oxidatively decomposed by the positive electrode material of the type; and consequently, the solvent in the electrolytic solution would be partly oxidatively decomposed on the positive electrode irrespective of the type of the positive electrode material, and as a result, there occurs a problem in that lithium ion movement is thereby retarded owing to deposition of decomposed products and gas generation and the battery characteristics, such as cycle properties and the like are thereby worsened.

Despite the situation, electronic appliances equipped with lithium secondary batteries therein are offering more and more an increasing range of functions and are being in a stream of further increase in power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of nonaqueous electrolytic solution may worsen battery performance at high temperatures.

PTL 1 proposes a nonaqueous electrolytic solution containing a phosphoric acid ester compound, such as triethylphosphonoacetate or the like, and indicates the possibility of enhancing continuous charging characteristics and high-temperature storage characteristics.

CITATION LIST

Patent Literature

PTL 1: WO2008/123038

SUMMARY OF THE INVENTION

Technical Problem

An object of the present invention is to provide a nonaqueous electrolytic solution capable of improving electrochemical characteristics at high temperatures, an energy storage device using it, and a specific organic phosphorus compound.

Solution to Problem

The present inventors have investigated in detail the performance of the nonaqueous electrolytic solutions in the above-mentioned prior art. As a result, the current situation is that the nonaqueous electrolytic solution of the above-mentioned patent literature could not be said to be sufficiently satisfactory for the problem of improving the cycle properties of batteries at high temperatures especially under high charging voltage.

Given the situation, the present inventors have assiduously studied for the purpose of solving the above-mentioned problems, and have found that, when at least one specific organic phosphorus compound is added to a nonaqueous electrolytic solution of an electrolyte salt dissolved in a non-aqueous solvent, then the electrochemical characteristics of energy storage devices, especially the cycle properties of lithium batteries at high temperatures can be improved, and have completed the present invention.

Specifically, the present invention provides the following (1) to (3):

(1) A nonaqueous electrolytic solution of an electrolyte salt dissolved in a non-aqueous solvent, which comprises at least one organic phosphorus compound represented by the following general formula (I):

[Chem. 1]

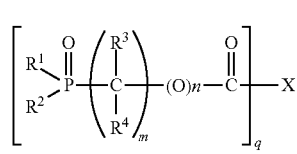
(I)

[Chem. 2]

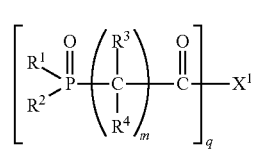
(II)

(In the formula, $R^1$ and $R^2$ each independently represent an alkyl group having from 1 to 6 carbon atoms, a cycloalkyl group having from 3 to 6 carbon atoms, an alkenyl group having from 2 to 6 carbon atoms, an alkynyl group having from 3 to 6 carbon atoms, an alkoxy group having from 1 to 6 carbon atoms, a cycloalkoxy group having from 3 to 6 carbon atoms, an alkenyloxy group having from 2 to 6 carbon atoms, an alkynyloxy group having from 3 to 6 carbon atoms, a halogenoalkyl group having from 1 to 6 carbon atoms, a halogenoalkoxy group having from 1 to 6 carbon atoms, an aryl group having from 6 to 12 carbon atoms in which at least one hydrogen atom may be substituted with a halogen atom, or an aryloxy group having from 6 to 12 carbon atoms in which at least one hydrogen atom may be substituted with a halogen atom, and in a case where $R^1$ and $R^2$ each are an alkyl group or an alkoxy group, $R^1$ and $R^2$ may bond to form a cyclic structure.

$R^3$ and $R^4$ each independently represent a hydrogen atom, a halogen atom, or an alkyl group having from 1 to 4 carbon atoms; m indicates an integer of from 1 to 4; n indicates 0 or 1; and q indicates 1 or 2.

In case where q is 1 and n is 0, X represents an alkoxy group having from 1 to 6 carbon atoms, an alkynyloxy group having from 3 to 6 carbon atoms, an alkyloxyalkoxy group having from 2 to 6 carbon atoms, an aryloxy group having from 6 to 12 carbon atoms in which at least one hydrogen atom may be substituted with a halogen atom, —O-L$^1$-OC(=O)—C(=O)—OR$^5$, —O-L$^2$-C(=O)—OR$^5$, or —O-L$^5$-CN; in case where q is 1 and n is 1, X represents an alkyl group having from 1 to 6 carbon atoms, an alkynyl group having from 2 to 6 carbon atoms, an alkoxy group having from 1 to 6 carbon atoms, an alkynyloxy group having from 3 to 6 carbon atoms, an alkyloxyalkoxy group having from 2 to 6 carbon atoms, or —C(=O)—OR$^5$; in case where q is 2, X represents —O-L$^3$-O—, —OC(=O)—C(=O)O— or a single bond. Further, R$^5$ represents an alkyl group having from 1 to 6 carbon atoms; L$^1$ and L$^3$ each represent an alkylene group having from 2 to 6 carbon atoms, or an alkynylene group having from 4 to 8 carbon atoms; L$^2$ and L$^5$ each represent an alkylene group having from 1 to 6 carbon atoms. However, when q is 1, n is 0 and X is an alkoxy group having from 1 to 6 carbon atoms, then R$^1$ and R$^2$ bond to form a cyclic structure; when q is 1, n is 0 and X is an aryloxy group having from 6 to 12 carbon atoms in which at least one hydrogen atom is substituted with a halogen atom, then R$^3$ and R$^4$ are both hydrogen atoms.)

(2) An energy storage device comprising a positive electrode, a negative electrode, and a nonaqueous electrolytic solution of an electrolyte salt dissolved in a non-aqueous solvent, wherein the nonaqueous electrolytic solution is the nonaqueous electrolytic solution of the above (1).

(3) An organic phosphorus compound represented by the following general formula (II):

(In the formula, $R^1$ and $R^2$ each independently represent an alkyl group having from 1 to 6 carbon atoms, a cycloalkyl group having from 3 to 6 carbon atoms, an alkenyl group having from 2 to 6 carbon atoms, an alkynyl group having from 3 to 6 carbon atoms, an alkoxy group having from 1 to 6 carbon atoms, a cycloalkoxy group having from 3 to 6 carbon atoms, an alkenyloxy group having from 2 to 6 carbon atoms, an alkynyloxy group having from 3 to 6 carbon atoms, a halogenoalkyl group having from 1 to 6 carbon atoms, a halogenoalkoxy group having from 1 to 6 carbon atoms, an aryl group having from 6 to 12 carbon atoms in which at least one hydrogen atom may be substituted with a halogen atom, or an aryloxy group having from 6 to 12 carbon atoms in which at least one hydrogen atom may be substituted with a halogen atom, and in a case where $R^1$ and $R^2$ each are an alkyl group or an alkoxy group, $R^1$ and $R^2$ may bond to form a cyclic structure.

$R^3$ and $R^4$ each independently represent a hydrogen atom, a halogen atom, or an alkyl group having from 1 to 4 carbon atoms; m indicates an integer of from 1 to 4; and q indicates 1 or 2. In case where q is 1, $X^1$ represents an alkynyloxy group having from 3 to 6 carbon atoms, an aryloxy group having from 7 to 12 carbon atoms in which at least one hydrogen atom on the benzene ring is substituted with a trifluoromethyl group, —O-L$^1$-OC(=O)—C(=O)—OR$^5$, O-L$^2$-C(=O)—OR$^5$, or —O-L$^5$-CN; in case where q is 2, $X^1$ represents —O-L$^4$-O—, or —OC(=O)—C(=O)O—. Further, R$^5$ represents an alkyl group having from 1 to 6 carbon atoms; L$^1$ represents an alkylene group having from 2 to 6 carbon atoms, or an alkynylene group having from 4 to 8 carbon atoms; L$^2$ and L$^5$ each represent an alkylene group having from 1 to 6 carbon atoms; and L$^4$ represents an alkynylene group having from 4 to 8 carbon atoms.)

Advantageous Effects of Invention

According to the present invention, there are provided a nonaqueous electrolytic solution capable of improving electrochemical characteristics at high temperatures, especially high-temperature cycle properties of energy storage devices, and an energy storage device, such as lithium batteries and others using the nonaqueous electrolytic solution.

DESCRIPTION OF EMBODIMENTS

The present invention relates to a nonaqueous electrolytic solution and an energy storage device using it.
[Nonaqueous Electrolytic Solution]
The nonaqueous electrolytic solution of the present invention comprises an electrolyte salt dissolved in a non-aqueous solvent, and comprises at least one organic phosphorus compound represented by the above-mentioned general formula (I).

Though not always clear, the reason why the nonaqueous electrolytic solution of the present invention can remarkably improve the cycle property of energy storage devices at high temperatures may be considered as follows:

The organic phosphorus compound in the present invention, as represented by the above-mentioned general formula (I), has three different substituents of a group P(=O)C—, a group C=O and a specific substituent X. The site of the substituent X forms a dense and highly heat-resistant surface film through decomposition on a positive electrode and a negative electrode, and on the other hand, the compound contains two different, relatively weakly electron-attractive substituents of P(=O)C— and C=O as the site that gently traps lithium ions inside the surface film, and therefore the lithium ion conductivity of the surface film greatly increases. Consequently, as compared with any other compound having only two of those three substituents, for example, triethylphosphonoacetate or the like compound having two, P(=O)C— and C=O of those substituents, the compound could attain the effect of remarkably improving high-temperature cycle properties, which, however, the other compounds that have two such substituents could not attain. In a case where $R^1$ and $R^2$ bond to form a ring and even when the substituent X is an alkoxy group in the case, the cyclic structure moiety to be formed by $R^1$ and $R^2$ bonding to each other can form a dense and highly heat-resistant surface film on a positive electrode and a negative electrode, and therefore it is considered that the compound of the case could also attain the same effect.

The organic phosphorus compound to be contained in the nonaqueous electrolytic solution of the present invention is represented by the following general formula (I):

[Chem. 3]

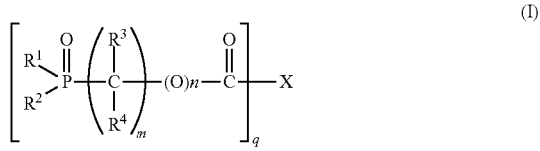

(I)

(In the formula, $R^1$ and $R^2$ each independently represent an alkyl group having from 1 to 6 carbon atoms, a cycloalkyl group having from 3 to 6 carbon atoms, an alkenyl group having from 2 to 6 carbon atoms, an alkynyl group having from 3 to 6 carbon atoms, an alkoxy group having from 1 to 6 carbon atoms, a cycloalkoxy group having from 3 to 6 carbon atoms, an alkenyloxy group having from 2 to 6 carbon atoms, an alkynyloxy group having from 3 to 6 carbon atoms, a halogenoalkyl group having from 1 to 6 carbon atoms, a halogenoalkoxy group having from 1 to 6 carbon atoms, an aryl group having from 6 to 12 carbon atoms in which at least one hydrogen atom may be substituted with a halogen atom, or an aryloxy group having from 6 to 12 carbon atoms in which at least one hydrogen atom may be substituted with a halogen atom, and in a case where $R^1$ and $R^2$ each are an alkyl group or an alkoxy group, $R^1$ and $R^2$ may bond to form a cyclic structure.

$R^3$ and $R^4$ each independently represent a hydrogen atom, a halogen atom, or an alkyl group having from 1 to 4 carbon atoms; m indicates an integer of from 1 to 4; n indicates 0 or 1; and q indicates 1 or 2.

In case where q is 1 and n is 0, X represents an alkoxy group having from 1 to 6 carbon atoms, an alkynyloxy group having from 3 to 6 carbon atoms, an alkyloxyalkoxy group having from 2 to 6 carbon atoms, or an aryloxy group having from 6 to 12 carbon atoms in which at least one hydrogen atom may be substituted with a halogen atom, —O-$L^1$-OC(=O)—C(=O)—$OR^5$, —O-$L^2$-C(=O)—$OR^5$, or —O-$L^5$-CN; incase where q is 1 and n is 1, X represents an alkyl group having from 1 to 6 carbon atoms, an alkynyl group having from 2 to 6 carbon atoms, an alkoxy group having from 1 to 6 carbon atoms, an alkynyloxy group having from 3 to 6 carbon atoms, an alkyloxyalkoxy group having from 2 to 6 carbon atoms, or —C(=O)—$OR^5$; in case where q is 2, X represents —O-$L^3$-O—, —OC(=O)—C(=O)O— or a single bond. Further, $R^5$ represents an alkyl group having from 1 to 6 carbon atoms; $L^1$ and $L^3$ each represent an alkylene group having from 2 to 6 carbon atoms, or an alkynylene group having from 4 to 8 carbon atoms; $L^2$ and $L^5$ each represent an alkylene group having from 1 to 6 carbon atoms. However, when q is 1, n is 0 and X is an alkoxy group having from 1 to 6 carbon atoms, then $R^1$ and $R^2$ bond to form a cyclic structure; when q is 1, n is 0 and X is an aryloxy group having from 6 to 12 carbon atoms in which at least one hydrogen atom is substituted with a halogen atom, then $R^3$ and $R^4$ are both hydrogen atoms.)

In the above-mentioned general formula (I), $R^1$ and $R^2$ each independently represent an alkyl group having from 1 to 6 carbon atoms, a cycloalkyl group having from 3 to 6 carbon atoms, an alkenyl group having from 2 to 6 carbon atoms, an alkynyl group having from 3 to 6 carbon atoms, an alkoxy group having from 1 to 6 carbon atoms, a cycloalkoxy group having from 3 to 6 carbon atoms, an alkenyloxy group having from 2 to 6 carbon atoms, an alkynyloxy group having from 3 to 6 carbon atoms, a halogenoalkyl group having from 1 to 6 carbon atoms in which at least one hydrogen atom is substituted with a halogen atom, a halogenoalkoxy group having from 1 to 6 carbon atoms, an aryl group having from 6 to 12 carbon atoms in which at least one hydrogen atom may be substituted with a halogen atom, or an aryloxy group having from 6 to 12 carbon atoms in which at least one hydrogen atom may be substituted with a halogen atom, and above all, preferably an alkyl group having from 1 to 6 carbon atoms, an alkoxy group having from 1 to 6 carbon atoms, or an alkynyloxy group having from 3 to 6 carbon atoms, more preferably an alkoxy group having 1 or 2 carbon atoms.

As specific examples of $R^1$ and $R^2$, preferably mentioned are a linear alkyl group, such as a methyl group, an ethyl group, an n-propyl group, an n-butyl group, an n-pentyl group, an n-hexyl group, etc.; a branched alkyl group, such as an iso-propyl group, a sec-butyl group, a tert-butyl group, a tert-amyl group, etc.; a cycloalkyl group, such as a cyclopropyl group, a cyclobutyl group, a cyclopentyl group, a cyclohexyl group, etc.; an alkenyl group, such as a 2-propenyl group, a 2-butenyl group, a 3-butenyl group, a 4-pentenyl group, a 5-hexenyl group, a 2-methyl-2-propenyl group, a 3-methyl-2-butenyl group, etc.; an alkynyl group, such as a 2-propynyl group, a 3-butynyl group, a 4-pentynyl group, a 5-hexynyl group, a 2-methyl-2-propynyl group, a 2,2-dimethyl-2-propynyl group, etc.; a linear alkoxy group, such as a methoxy group, an ethoxy group, an n-propoxy group, an n-butoxy group, an n-pentyloxy group, an n-hexyloxy group, etc.; a branched alkoxy group, such as an iso-propoxy group, a sec-butoxy group, a tert-butoxy group, a tert-amyloxy group, etc.; a cycloalkoxy group, such as a cyclopropyloxy group, a cyclobutyloxy group, a cyclopentyloxy group, a cyclohexyloxy group, etc.; an alkenyloxy group, such as a 2-propenyloxy group, a 2-butenyloxy group, a 3-butenyloxy group, a 4-pentenyloxy group, a 5-hexenyloxy group, etc.; an alkynyloxy group, such as a 2-propynyloxy group, a 3-butynyloxy group, a 4-pentynyloxy group, a 5-hexynyloxy group, a 2-methyl-2-propenyloxy group, a 3-methyl-2-butenyloxy group, etc.; an alkynyloxy group, such as a 2-propynyloxy group, a 3-butynyloxy group, a 4-pentynyloxy group, a 5-hexynyloxy group, a 2-methyl-2-propynyloxy group, a 2,2-dimethyl-2-propynyloxy group, etc.; an alkyl group in which the hydrogen atom is partly substituted with a fluorine atom, such as a fluoromethyl group, a trifluoromethyl group, a 2,2,2-trifluoroethyl group, etc.; an alkoxy group in which the hydrogen atom is partly substituted with a fluorine atom, such as a fluoromethoxy group, a trifluoromethoxy group, a 2,2,2-trifluoroethoxy group, etc.; an aryl group, such as a phenyl group, a 2-methylphenyl group, a 3-methylphenyl group, a 4-methylphenyl group, a 4-tert-butylphenyl group, a 2,4,6-trimethylphenyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 2,4,6-trifluorophenyl group, a pentafluorophenyl group, a 4-trifluoromethylphenyl group, etc.; an aryloxy group, such as a phenyloxy group, a 2-methylphenyloxy group, a 3-methylphenyloxy group, a 4-methylphenyloxy group, a 4-tert-butylphenyloxy group, a 2,4,6-trimethylphenyloxy group, a 2-fluorophenyloxy group, a 3-fluorophenyloxy group, a 4-fluorophenyloxy group, a 2,4-difluorophenyloxy group, a 2,6-difluorophenyloxy group, a 3,4-difluorophenyloxy group, a 2,4,6-trifluorophenyloxy group, a pentafluorophenyloxy group, a 4-trifluoromethylphenyloxy group, etc.; a substituent to form a ring with $R^1$ and $R^2$, such a butane-1,4-diyl group, a pentane-1,5-diyl group, —$(CH_2)_3O$—, —$(CH_2)_4O$—, an ethane-1,2-dioxy group, a propane-1,2-dioxy group, a propane-1,3-dioxy group, a butane-2,3-dioxy group, etc. Of those, preferred are a methyl group, an ethyl group, an n-propyl group, an n-butyl group, a methoxy group, an ethoxy group, an n-propoxy group, an n-butoxy group, a phenyl group, a phenyloxy group, and an ethane-1,2-dioxy group; and more preferred are a methoxy group, and an ethoxy group.

In a case where q is 1, n is 0 and X is an alkoxy group having from 1 to 6 carbon atoms, $R^1$ and $R^2$ may bond to form a cyclic structure.

$R^3$ and $R^4$ each independently represent a hydrogen atom, a halogen atom, or an alkyl group having from 1 to 4 carbon atoms; and above all, each is preferably a hydrogen atom, or an alkyl group having from 1 to 4 carbon atoms.

As specific examples of $R^3$ and $R^4$, preferably mentioned are a hydrogen atom, a fluorine atom, a chlorine atom, a bromine atom, a methyl group, an ethyl group, an n-propyl group, an n-butyl group, an n-pentyl group, an n-hexyl group, an iso-propyl group, a sec-butyl group, and a tert-butyl group; and above all, preferred are a hydrogen atom, a fluorine atom, a methyl group and an ethyl group, and more preferred is a hydrogen atom.

When q is 1, n is 0 and X is an aryloxy group having from 6 to 12 carbon atoms in which at least one hydrogen atom is substituted with a halogen atom, then $R^3$ and $R^4$ are both hydrogen atoms.

m indicates an integer of from 1 to 4, n indicates 0 or 1, and q indicates 1 or 2. m is preferably 1 or 2, n is preferably 0, and q is preferably 2.

In case where q is 1 and n is 0, X represents an alkoxy group having from 1 to 6 carbon atoms, an alkynyloxy group having from 3 to 6 carbon atoms, an alkyloxyalkoxy group having from 2 to 6 carbon atoms, an aryloxy group having from 6 to 12 carbon atoms in which at least one hydrogen atom may be substituted with a halogen atom, —O-$L^1$-OC(=O)—C(=O)—O$R^5$, —O-$L^2$-C(=O)—O$R^5$, or —O-$L^5$-CN, and above all, X is preferably an alkynyloxy group having from 3 to 6 carbon atoms, an aryloxy group having from 6 to 12 carbon atoms in which at least one hydrogen atom is substituted with a halogen atom, or —O-$L^2$-C(=O)—O$R^5$.

In case where q is 1 and n is 1, X represents an alkyl group having from 1 to 6 carbon atoms, an alkynyl group having from 2 to 6 carbon atoms, an alkoxy group having from 1 to 6 carbon atoms, an alkynyloxy group having from 3 to 6 carbon atoms, an alkyloxyalkoxy group having from 2 to 6 carbon atoms, or —C(=O)—O$R^5$, and above all, X is preferably —C(=O)—O$R^5$.

In case where q is 2, X represents —O-$L^3$-O—, —OC(=O)—C(=O)O— or a single bond. Above all, X is preferably —O-$L^3$-O—.

Further, $L^1$ and $L^3$ each represent an alkylene group having from 2 to 6 carbon atoms, or an alkynylene group having from 4 to 8 carbon atoms; $L^2$ and $L^5$ each represent an alkylene group having from 1 to 6 carbon atoms.

As specific examples of $L^1$ and $L^3$, preferably mentioned are an ethane-1,2-diyl group, a propane-1,3-diyl group, a propane-1,2-diyl group, a butane-1,4-diyl group, a butane-2,3-diyl group, a 2-butyne-1,4-diyl group, a 3-hexyne-2,5-diyl group, and a 2,5-dimethyl-3-hexyne-2,5-diyl group; and above all, preferred are an ethane-1,2-diyl group, a propane-1,3-diyl group, a butane-2,3-diyl group, and a 2-butyne-1,4-diyl group.

As specific examples of $L^2$ and $L^5$, preferably mentioned are a methylene group, an ethane-1,2-diyl group, an ethane-1,1-diyl group, a propane-1,3-diyl group, a propane-1,1-diyl group, a propane-1,2-diyl group, a butane-1,4-diyl group, a butane-1,1-diyl group, and a butane-1,2-diyl group; and above all, preferred are a methylene group, an ethane-1,2-diyl group, and an ethane-1,1-diyl group.

As specific examples of $R^5$, preferably mentioned are a linear alkyl group, such as a methyl group, an ethyl group, an n-propyl group, an n-butyl group, an n-pentyl group, an n-hexyl group, etc.; and a branched alkyl group, such as an iso-propyl group, a sec-butyl group, a tert-butyl group, a tert-amyl group, etc.; and above all, preferred are a methyl group and an ethyl group.

Specific examples of X are mentioned below.

(i) In the case where q is 1 and n is 0:

X is preferably a linear alkyloxy group, such as a methoxy group, an ethoxy group, an n-propoxy group, an n-butoxy group, an n-pentoxy group, an n-hexyloxy group, etc.; a branched alkyloxy group, such as an iso-propoxy group, a sec-butoxy group, a tert-butoxy group, a tert-amyloxy group, etc.; an alkynyloxy group, such as a 2-propynyloxy group, a 2-butynyloxy group, a 3-butynyloxy group, a 4-pentynyloxy group, a 5-hexynyloxy group, a 1-methyl-2-propynyloxy group, a 1-methyl-2-butynyloxy group, a 1,1-dimethyl-2-propynyloxy group, etc.; an alkyloxyalkoxy group, such as a 2-methoxyethoxy group, a 2-ethoxyethoxy group, a 2-butoxyethoxy group, a 2-methoxypropoxy group, a 3-methoxypropoxy group, etc.; a phenoxy group in which at least one hydrogen atom is substituted with a halogen atom, such as a 2-fluorophenoxy group, a 3-fluorophenoxy group, a 4-fluorophenoxy group, a 2,4-difluorophenoxy group, a 3,5-difluorophenoxy group, a 2,3,5-trifluorophenoxy group, a 2,4,6-trifluorophenoxy group, a 2,3,5,6-tetrafluorophenoxy group, a pentafluorophenoxy group, a 2-trifluoromethylphenoxy group, a 3-trifluoromethylphenoxy group, a 4-trifluoromethylphenoxy group, a 2,4-bis(trifluoromethyl)phenoxy group, a 3,5-bis(trifluoromethyl)phenoxy group, a 2-chlorophenoxy group, a 3-chlorophenoxy group, a 4-chlorophenoxy group, a 2,4-dichlorophenoxy group, a 3,5-dichlorophenoxy group, a 2,3,5-trichlorophenoxy group, a 2,4,6-trichlorophenoxy group, a 2,3,5,6-tetrachlorophenoxy group, a pentachlorophenoxy group, a 2-trichloromethylphenoxy group, a 3-trichloromethylphenoxy group, a 4-trichloromethylphenoxy group, a 2,4-bis(trichloromethyl)phenoxy group, a 3,5-bis(trichloromethyl)phenoxy group, etc.; an alkoxy group having an oxalate structure, such as —$OCH_2CH_2OC(=O)$—$C(=O)OCH_3$, —$OCH_2CH_2OC(=O)$—$C(=O)OCH_2CH_3$, —OCH₂CH₂CH₂OC(=O)—C(=O)OCH₃, —OCH₂CH₂CH₂OC(=O)—C(=O)OCH₂CH₃, etc.; an alkynyloxy group having an oxalate structure, such as —OCH₂C≡CCH₂OC(=O)—C(=O)OCH₃, —OCH₂C≡CCH₂OC(=O)—C(=O)OCH₂CH₃, etc.; an alkoxy group having an alkoxycarbonyl group, such as —OCH₂C(=O)OCH₃, —OCH₂(C=O)OCH₂CH₃, —OCH(CH₃)C(=O)OCH₃, —OCH(CH₃)C(=O)OCH₂CH₃, —OCH(CH₂CH₃)C(=O)OCH₃, —OCH(CH₂CH₃)C(=O)OCH₂CH₃, etc.; or an alkoxy group having a cyano group, such as —OCH₂CN, —OCH₂CH₂CN, —OCH(CH₃)CN, —OCH₂CH₂CH₂CN, —OCH(CH₂CH₃)CN, —OCH₂CH₂CH₂CH₂CN, etc. Above all, preferred is a 2-propynyloxy group, a 1-methyl-2-propynyloxy group, a 1,1-dimethyl-2-propynyloxy group, a 2-trifluoromethylphenoxy group, a 4-trifluoromethylphenoxy group, —OCH₂C(=O)OCH₃, —OCH₂C(=O)OCH₂CH₃, —OCH(CH₃)C(=O)OCH₃, or OCH(CH₃)C(=O)OCH₂CH₃; and more preferred is a 2-propynyloxy group, —OCH₂C(=O)OCH₃, —OCH₂C(=O) OCH₂CH₃, —OCH(CH₃)C(=O)OCH₃, —OCH(CH₃)C(=O)OCH₂CH₃, —OCH₂CN, —OCH₂CH₂CN, or —OCH(CH₃)CN.

(ii) In the case where q is 1 and n is 1:

X is preferably a linear alkyl group, such as a methyl group, an ethyl group, an n-propyl group, an n-butyl group, an n-pentyl group, an n-hexyl group, etc.; a branched alkyl group, such as an iso-propyl group, a sec-butyl group, a tert-butyl group, a tert-amyl group, etc.; an alkynyl group, such as an ethynyl group, a 2-propynyl group, a 2-butynyl group, a 3-butynyl group, etc.; a linear alkyloxy group, such as a methoxy group, an ethoxy group, an n-propoxy group, an n-butoxy group, an n-pentyloxy group, an n-hexyloxy group, etc.; a branched alkyloxy group, such as an iso-propoxy group, a sec-butoxy group, a tert-butoxy group, a tert-amyloxy group, etc.; an alkyloxyalkoxy group, such as a 2-methoxyethoxy group, a 2-ethoxyethoxy group, a 2-butoxyethoxy group, a 2-methoxypropoxy group, a 3-methoxypropoxy group, etc.; or an alkoxycarbonyl group, such as —C(=O)—OCH₃, —C(=O)—OCH₂CH₃, etc. Above all, preferred is a methyl group, an ethyl group, an n-propyl group, an ethynyl group, a 2-propynyl group, a methoxy group, an ethoxy group, a 2-methoxyethoxy group, a 2-ethoxyethoxy group, —C(=O)—OCH₃, or —C(=O)—OCH₂CH₃; and more preferred is a methyl group, an ethyl group, an ethynyl group, a 2-propynyl group, —C(=O)—OCH₃, or —C(=O)—OCH₂CH₃.

(iii) In the case where q is 2:

X is preferably an alkanedioxy group, such as an ethane-1,2-dioxy group, a propane-1,2-dioxy group, a propane-1,3-dioxy group, a butane-1,4-dioxy group, a butane-2,3-dioxy group, etc.; an alkynedioxy group, such as a 2-butyne-1,4-dioxy group, a 3-hexyne-2,5-dioxy group, a 2,5-dimethyl-3-hexyne-2,5-dioxy group, etc.; —C(=O)—C(=O)—, a single bond, etc. Above all, preferred is an ethane-1,2-dioxy group, a 2-butyne-1,4-dioxy group, or a single bond.

Specific examples of the organic phosphorus compound represented by the above-mentioned general formula (I) are mentioned below.

(i) As the case where q is 1 and n is 0:

Preferably mentioned are 2-propynyl 2-(dimethylphosphoryl)acetate, 1-methyl-2-propynyl 2-(dimethylphosphoryl)acetate, 1,1-dimethyl-2-propynyl 2-(dimethylphosphoryl)acetate, 2-propynyl 2-(diethylphosphoryl)acetate, 1-methyl-2-propynyl 2-(diethylphosphoryl)acetate, 1,1-dimethyl-2-propynyl 2-(diethylphosphoryl)acetate, 2-propynyl 2-(dipropylphosphoryl)acetate, 1-methyl-2-propynyl 2-(dipropylphosphoryl)acetate, 1,1-dimethyl-2-propynyl 2-(dipropylphosphoryl)acetate, 2-propynyl 2-(dibutylphosphoryl)acetate, 1-methyl-2-propynyl 2-(dibutylphosphoryl)acetate, 1,1-dimethyl-2-propynyl 2-(dibutylphosphoryl)acetate, 2-propynyl 2-(di-isopropylphosphoryl)acetate, 1-methyl-2-propynyl 2-(di-isopropylphosphoryl)acetate, 1,1-dimethyl-2-propynyl 2-(di-isopropylphosphoryl)acetate, 2-propynyl 2-(dicyclopropylphosphoryl)acetate, 2-propynyl 2-(dicyclobutylphosphoryl)acetate, 2-propynyl 2-(dicyclopentylphosphoryl)acetate, 2-propynyl 2-(dicyclohexylphosphoryl)acetate, 1-methyl-2-propynyl 2-(dicyclohexylphosphoryl)acetate, 1,1-dimethyl-2-propynyl 2-(dicyclohexylphosphoryl)acetate, 2-propynyl 2-(di(2-propenyl)phosphoryl)acetate, 1-methyl-2-propynyl 2-(di(2-propenyl)phosphoryl)acetate, 1,1-dimethyl-2-propynyl 2-(di(2-propenyl)phosphoryl)acetate, 2-propynyl 2-(di(2-butenyl)phosphoryl)acetate, 1-methyl-2-propynyl 2-(di(2-butenyl)phosphoryl)acetate, 1,1-dimethyl-2-propynyl 2-(di(2-butenyl)phosphoryl)acetate, 2-propynyl 2-(di(3-butenyl)phosphoryl)acetate, 2-propynyl 2-(di(4-pentenyl)phosphoryl)acetate, 2-propynyl 2-(di(5-hexenyl)phosphoryl)acetate, 2-propynyl 2-(bis(2-methyl-2-propenyl)phosphoryl)acetate, 2-propynyl 2-(bis(3-methyl-2-butenyl)phosphoryl)acetate, 2-propynyl 2-(di(2-propynyl)phosphoryl)acetate, 1-methyl-2-propynyl 2-(di(2-propynyl)phosphoryl)acetate, 1,1-dimethyl-2-propynyl 2-(di(2-propynyl)phosphoryl)acetate, 2-propynyl 2-(di(3-butynyl)phosphoryl)acetate, 2-propynyl 2-(di(4-pentynyl)phosphoryl)acetate, 2-propynyl 2-(di(5-hexynyl)phosphoryl)acetate, 2-propynyl 2-(bis(1-methyl-2-propynyl)phosphoryl)acetate, 2-propynyl 2-(bis(1,1-dimethyl-2-propynyl)phosphoryl)acetate, 2-propynyl 2-(bis(3,3,3-trifluoroethyl)phosphoryl)acetate, 1-methyl-2-propynyl 2-(bis(3,3,3-trifluoroethyl)phosphoryl)acetate, 1,1-dimethyl-2-propynyl 2-(bis(3,3,3-trifluoroethyl)phosphoryl)acetate, 2-propynyl 2-(diphenylphosphoryl)acetate, 1-methyl-2-propynyl 2-(diphenylphosphoryl)acetate, 1,1-dimethyl-2-propynyl 2-(diphenylphosphoryl)acetate, 2-propynyl 2-(bis(4-methylphenyl)phosphoryl)acetate, 1-methyl-2-propynyl 2-(bis(4-methylphenyl)phosphoryl)acetate, 1,1-dimethyl-2-propynyl 2-(bis(4-methylphenyl)phosphoryl)acetate, 2-propynyl 2-(bis(4-fluorophenyl)phosphoryl)acetate, 1-methyl-2-propynyl 2-(bis(4-fluorophenyl)phosphoryl)acetate, 1,1-dimethyl-2-propynyl 2-(bis(4-fluorophenyl)phosphoryl)acetate, 2-propynyl 2-(dimethylphosphoryl)propanoate, 2-propynyl 2-(diethylphosphoryl)propanoate, 2-propynyl 2-(diphenylphosphoryl)propanoate, 2-propynyl 2-(dimethylphosphoryl)butanoate, 2-propynyl 2-(diethylphosphoryl)butanoate, 2-propynyl 2-(diphenylphosphoryl)butanoate, 2-propynyl 3-(dimethylphosphoryl)propanoate, 2-propynyl 3-(diethylphosphoryl)propanoate, 2-propynyl 3-(diphenylphosphoryl)propanoate, 2-propynyl 4-(dimethylphosphoryl)butanoate, 2-propynyl 4-(diethylphosphoryl)butanoate, 2-propynyl 4-(diphenylphosphoryl)butanoate, 2-propynyl 2-(dimethylphosphoryl)-2-fluoroacetate, 2-propynyl 2-(diethylphosphoryl)-2-fluoroacetate, 2-propynyl 2-(diphenylphosphoryl)-2-fluoroacetate, 2-propynyl 2-(methoxy(methyl)phosphoryl)acetate, 1-methyl-2-propynyl 2-(methoxy(methyl)phosphoryl)acetate, 1,1-dimethyl-2-propynyl 2-(methoxy(methyl)phosphoryl)acetate, 2-propynyl 2-(ethoxy(ethyl)phosphoryl)acetate, 1-methyl-2-propynyl 2-(ethoxy(ethyl)phosphoryl)acetate, 1,1-dimethyl-2-propynyl 2-(ethoxy(ethyl)phosphoryl)acetate, 2-propynyl 2-(cyclohexyloxy(methyl)phosphoryl)acetate, 2-propynyl 2-(methyl(2-propenyloxy)phosphoryl)acetate, 2-propynyl 2-(methyl(2-propynyloxy)phosphoryl)acetate, 2-propynyl 2-(methoxy(methyl)phosphoryl)propanoate, 2-propynyl 2-(ethoxy(ethyl)phosphoryl)propanoate, 2-propynyl 2-(methoxy(methyl)phosphoryl)butanoate, 2-propynyl 2-(ethoxy(ethyl)phosphoryl)butanoate, 2-propynyl 3-(methoxy(methyl)phosphoryl)propanoate, 2-propynyl 3-(ethoxy(ethyl)phosphoryl)propanoate, 2-propynyl 4-(methoxy(methyl)phosphoryl)butanoate, 2-propynyl 4-(ethoxy(ethyl)phosphoryl)butanoate, 2-propynyl 2-(methoxy(methyl)phosphoryl)-2-fluoroacetate, 2-propynyl 2-(ethoxy(ethyl)phosphoryl)-2-fluoroacetate, 2-propynyl 2-(dimethoxyphosphoryl)acetate, 2-butynyl 2-(dimethoxyphosphoryl)acetate, 3-butynyl 2-(dimethoxyphosphoryl)acetate, 4-pentynyl 2-(dimethoxyphosphoryl)acetate, 5-hexynyl 2-(dimethoxyphosphoryl)acetate, 1-methyl-2-propynyl 2-(dimethoxyphosphoryl)acetate, 1-methyl-2-butynyl 2-(dimethoxyphosphoryl)acetate, 1,1-dimethyl-2-propynyl 2-(dimethoxyphosphoryl)acetate, 2-propynyl 2-(diethoxyphosphoryl)acetate, 2-butynyl 2-(diethoxyphosphoryl)acetate, 3-butynyl 2-(diethoxyphosphoryl)acetate, 4-pentynyl 2-(diethoxyphosphoryl)acetate, 5-hexynyl 2-(diethoxyphosphoryl)acetate, 1-methyl-2-propynyl 2-(diethoxyphosphoryl)acetate, 1-methyl-2-butynyl 2-(diethoxyphosphoryl)acetate, 1,1-dimethyl-2-propynyl 2-(diethoxyphosphoryl)acetate, 2-propynyl 2-(dipropoxyphosphoryl)acetate, 1-methyl-2-propynyl 2-(dipropoxyphosphoryl)acetate, 1,1-dimethyl-2-propynyl 2-(dipropoxyphosphoryl)acetate, 2-propynyl 2-(dibutoxyphosphoryl)acetate, 1-methyl-2-propynyl 2-(dibutoxyphosphoryl)acetate, 1,1-dimethyl-2-propynyl 2-(dibutoxyphosphoryl)acetate, 2-propynyl 2-(di-isopropoxyphosphoryl)acetate, 1-methyl-2-propynyl 2-(di-isopropoxyphosphoryl)acetate, 1,1-dimethyl-2-propynyl 2-(di-isopropoxyphosphoryl)acetate, 2-propynyl 2-(di(cyclopropyloxy)phosphoryl)acetate, 2-propynyl 2-(di(cyclobutyloxy)phosphoryl)acetate, 2-propynyl 2-(di(cyclopentyloxy)phosphoryl)acetate, 2-propynyl 2-(di(cyclohexyloxy)phosphoryl)acetate, 1-methyl-2-propynyl 2-(di(cyclohexyloxy)phosphoryl)acetate, 1,1-dimethyl-2-propynyl 2-(di(cyclohexyloxy)phosphoryl)acetate, 2-propynyl 2-(di(2-propenyloxy)phosphoryl)acetate, 1-methyl-2-propynyl 2-(di(2-propenyloxy)phosphoryl)acetate, 1,1-dimethyl-2-propynyl 2-(di(2-propenyloxy)phosphoryl)acetate, 2-propynyl 2-(di(2-butenyloxy)phosphoryl)acetate, 1-methyl-2-propynyl 2-(di(2-butenyloxy)phosphoryl)acetate, 1,1-dimethyl-2-propynyl 2-(di(2-butenyloxy)phosphoryl)acetate, 2-propynyl 2-(di(3-butenyloxy)phosphoryl)acetate, 2-propynyl 2-(di(4-pentenyloxy)phosphoryl)acetate, 2-propynyl 2-(di(5-hexenyloxy)phosphoryl)acetate, 2-propynyl 2-(bis(2-methyl-2-propenyloxy)phosphoryl)acetate, 2-propynyl 2-(bis(3-methyl-2-butenyloxy)phosphoryl)acetate, 2-propynyl 2-(di(2-propynyloxy)phosphoryl)acetate, 1-methyl-2-propynyl 2-(di(2-propynyloxy)phosphoryl)acetate, 1,1-dimethyl-2-propynyl 2-(di(2-propynyloxy)phosphoryl)acetate, 2-propynyl 2-(di(3-butynyloxy)phosphoryl)acetate, 2-propynyl 2-(di(4-pentynyloxy)phosphoryl)acetate, 2-propynyl 2-(di(5-hexynyloxy)phosphoryl)acetate, 2-propynyl 2-(bis(1-methyl-2-propynyloxy)phosphoryl)acetate, 2-propynyl 2-(bis(1,1-dimethyl-2-propynyloxy)phosphoryl)acetate, 2-propynyl 2-(bis(3,3,3-trifluoroethoxy)phosphoryl)acetate, 1-methyl-2-propynyl 2-(bis(3,3,3-trifluoroethoxy)phosphoryl)acetate, 1,1-dimethyl-2-propynyl 2-(bis(3,3,3-trifluoroethoxy)phosphoryl)acetate, 2-propynyl 2-(diphenoxyphosphoryl)acetate, 1-methyl-2-propynyl 2-(diphenoxyphosphoryl)acetate, 1,1-dimethyl-2-propynyl 2-(diphenoxyphosphoryl)acetate, 2-propynyl 2-(bis(4-methylphenoxy)phosphoryl)acetate, 1-methyl-2-propynyl 2-(bis(4-methylphenoxy)phosphoryl)acetate, 1,1-dimethyl-2-propynyl 2-(bis(4-methylphenoxy))acetate, 2-propynyl 2-(bis(4-fluorophenoxy)phosphoryl)acetate, 1-methyl-2-propynyl 2-(bis(4-fluorophenoxy)phosphoryl)acetate, 1,1-dimethyl-2-propynyl 2-(bis(4-fluorophenoxy)phosphoryl)acetate, 2-propynyl 2-(dimethoxyphosphoryl)propanoate, 2-propynyl 2-(diethoxyphosphoryl)propanoate, 2-propynyl 2-(diphenoxyphosphoryl)propanoate, 2-propynyl 2-(dimethoxyphosphoryl)butanoate, 2-propynyl 2-(diethoxyphosphoryl)butanoate, 2-propynyl 2-(diphenoxyphosphoryl)butanoate, 2-propynyl 3-(dimethoxyphosphoryl)propanoate, 2-propynyl 3-(diethoxyphosphoryl)propanoate, 2-propynyl 3-(diphenoxyphosphoryl)propanoate, 2-propynyl 4-(dimethoxyphosphoryl)butanoate, 2-propynyl 4-(diethoxyphosphoryl)butanoate, 2-propynyl 4-(diphenoxyphosphoryl)butanoate, 2-propynyl 2-(dimethoxyphosphoryl)-2-fluoroacetate, 2-propynyl 2-(diethoxyphosphoryl)-2-fluoroacetate, 2-propynyl 2-(diphenoxyphosphoryl)-2-fluoroacetate, 2-methoxyethyl 2-(dimethoxyphosphoryl)acetate, 2-ethoxyethyl 2-(dimethoxyphosphoryl)acetate, 2-butoxyethyl 2-(dimethoxyphosphoryl)acetate, 2-methoxypropyl 2-(dimethoxyphosphoryl)acetate, 3-methoxypropyl 2-(dimethoxyphosphoryl)acetate, 2-methoxyethyl 2-(diethoxyphosphoryl)acetate, 2-ethoxyethyl 2-(diethoxyphosphoryl)acetate, 2-butoxyethyl 2-(diethoxyphosphoryl)acetate, 2-methoxypropyl 2-(diethoxyphosphoryl)acetate, 3-methoxypropyl 2-(diethoxyphosphoryl)acetate, 2-fluorophenyl 2-(dimethoxyphosphoryl)acetate, 2-fluorophenyl 2-(diethoxyphosphoryl)acetate, 4-fluorophenyl 2-(dimethoxyphosphoryl)acetate, 4-fluorophenyl 2-(diethoxyphosphoryl)acetate, 2,4-difluorophenyl 2-(dimethoxyphosphoryl)acetate, 2,4-difluorophenyl 2-(diethoxyphosphoryl)acetate, 2,4,6-trifluorophenyl 2-(dimethoxyphosphoryl)acetate, 2,4,6-trifluorophenyl 2-(diethoxyphosphoryl)acetate, pentafluorophenyl 2-(dimethoxyphosphoryl)acetate, pentafluorophenyl 2-(diethoxyphosphoryl)acetate, 2-trifluoromethylphenyl 2-(dimethoxyphosphoryl)acetate, 2-trifluoromethylphenyl 2-(diethoxyphosphoryl)acetate, 3-trifluoromethylphenyl 2-(dimethoxyphosphoryl)acetate, 3-trifluoromethylphenyl 2-(diethoxyphosphoryl)acetate, 4-trifluoromethylphenyl 2-(dimethoxyphosphoryl)acetate, 4-trifluoromethylphenyl 2-(diethoxyphosphoryl)acetate, 2,4-bis(trifluoromethyl)phenyl 2-(dimethoxyphosphoryl)acetate, 2,4-bis(trifluoromethyl)phenyl 2-(diethoxyphosphoryl)acetate, 3,5-bis(trifluoromethyl)phenyl 2-(dimethoxyphosphoryl)acetate, 3,5-bis(trifluoromethyl)phenyl 2-(diethoxyphosphoryl)acetate, 2-chlorophenyl 2-(dimethoxyphosphoryl)acetate, 2-chlorophenyl 2-(diethoxyphosphoryl)acetate, 4-chlorophenyl 2-(dimethoxyphosphoryl)acetate, 4-chlorophenyl 2-(diethoxyphosphoryl)acetate, 2,4-dichlorophenyl 2-(dimethoxyphosphoryl)acetate, 2,4-dichlorophenyl 2-(diethoxyphosphoryl)acetate, 2,4,6-trichlorophenyl 2-(dimethoxyphosphoryl)acetate, 2,4,6-trichlorophenyl 2-(diethoxyphosphoryl)acetate, pentachlorophenyl 2-(dimethoxyphosphoryl)acetate, pentachlorophenyl 2-(diethoxyphosphoryl)acetate, 2-trichloromethylphenyl 2-(dimethoxyphosphoryl)acetate, 2-trichloromethylphenyl 2-(diethoxyphosphoryl)acetate, 3-trichloromethylphenyl 2-(dimethoxyphosphoryl)acetate, 3-trichloromethylphenyl 2-(diethoxyphosphoryl)acetate, 4-trichloromethylphenyl 2-(dimethoxyphosphoryl)acetate, 4-trichloromethylphenyl 2-(diethoxyphosphoryl)acetate, 2,4-bis(trichloromethyl)phenyl 2-(dimethoxyphosphoryl)acetate, 2,4-bis(trichloromethyl)phenyl 2-(diethoxyphosphoryl)acetate, 3,5-bis(trichloromethyl)phenyl 2-(dimethoxyphosphoryl)acetate, 3,5-bis(trichloromethyl)phenyl 2-(diethoxyphosphoryl)acetate, 2-(2-(dimethoxyphosphoryl)acetoxy)ethyl methyl oxalate, 2-(2-(dimethoxyphosphoryl)acetoxy)ethyl ethyl oxalate, 2-(2-(diethoxyphosphoryl)acetoxy)ethyl methyl oxalate, 2-(2-(diethoxyphosphoryl)acetoxy)ethyl ethyl oxalate, 2-(3-(diethoethoxyphosphoryl)acetoxy)propyl methyl oxalate, 2-(3-(diethoxyphosphoryl)acetoxy)propyl ethyl oxalate, 4-(2-(diethoxyphosphoryl)acetoxy)-2-butyn-1-yl methyl oxalate, 4-(2-(diethoxyphosphoryl)acetoxy)-2-butyn-1-yl ethyl oxalate, methyl 2-((diethoxyphosphoryl)acetoxy)acetate, ethyl 2-((diethoxyphosphoryl)acetoxy)acetate, methyl 2-(2-(dimethoxyphosphoryl)acetoxy)propanoate, ethyl 2-(2-(dimethoxyphosphoryl)acetoxy)propanoate, methyl 2-(2-(diethoxyphosphoryl)acetoxy)propanoate, ethyl 2-(2-(diethoxyphosphoryl)acetoxy)propanoate, methyl 2-(2-(diethoxyphosphoryl)acetoxy)butanoate, ethyl 2-(2-(diethoxyphosphoryl)acetoxy)butanoate, cyanomethyl 2-(dimethoxyphosphoryl)acetate, cyanomethyl 2-(diethoxyphosphoryl)acetate, 2-cyanoethyl 2-(dimethoxyphosphoryl)acetate, 2-cyanoethyl 2-(diethoxyphosphoryl)acetate, 1-cyanoethyl 2-(diethoxyphosphoryl)acetate, 3-cyanopropyl 2-(diethoxyphosphoryl)acetate, 1-cyanopropyl 2-(diethoxyphosphoryl)acetate, 4-cyanobutyl 2-(diethoxyphosphoryl)acetate, etc.

Further, as preferred examples of the compound where (i) q is 1 and n is 0 and where $R^1$ and $R^2$ form a ring, there are mentioned methyl 2-(1-oxidophospholan-1-yl)acetate, ethyl 2-(1-oxidophospholan-1-yl)acetate, 2-propynyl 2-(1-oxidophospholan-1-yl)acetate, methyl 2-(1-oxidophosphorinan-1-yl)acetate, ethyl 2-(1-oxidophosphorinan-1-yl)acetate, 2-propynyl 2-(1-oxidophosphorinan-1-yl)acetate, methyl 2-(2-oxido-1,2-oxaphospholan-2-yl)acetate, ethyl 2-(2-oxido-1,2-oxaphospholan-2-yl)acetate, 2-propynyl 2-(2-oxido-1,2-oxaphospholan-2-yl)acetate, methyl 2-(2-oxido-1,2-oxaphosphorinan-2-yl)acetate, ethyl 2-(2-oxido-1,2-oxaphosphorinan-2-yl)acetate, 2-propynyl 2-(2-oxido-1,2-oxaphosphorinan-2-yl)acetate, methyl 2-(2-oxido-1,3,2-dioxaphospholan-2-yl)acetate, ethyl 2-(2-oxido-1,3,2-dioxaphospholan-2-yl)acetate, 2-propynyl 2-(2-oxido-1,3,2-dioxaphospholan-2-yl)acetate, methyl 2-(2-oxido-1,3,2-dioxaphosphorinan-2-yl)acetate, ethyl 2-(2-oxido-1,3,2-dioxaphosphorinan-2-yl)acetate, 2-propynyl 2-(2-oxido-1,3,2-dioxaphosphorinan-2-yl)acetate, methyl 2-(4,5-dimethyl-2-oxido-1,3,2-dioxaphospholan-2-yl)acetate, ethyl 2-(4,5-dimethyl-2-oxido-1,3,2-dioxaphospholan-2-yl)acetate, 2-propynyl 2-(4,5-dimethyl-2-oxido-1,3,2-dioxaphospholan-2-yl)acetate, etc.

(ii) As the case where q is 1 and n is 1:

Preferably mentioned are (dimethoxyphosphoryl)methyl acetate, (diethoxyphosphoryl)methyl acetate, (dimethoxyphosphoryl)methyl propanoate, (diethoxyphosphoryl)methyl propanoate, (dimethoxyphosphoryl)methyl butanoate, (diethoxyphosphoryl)methyl butanoate, (dimethoxyphosphoryl)methyl isobutyrate, (diethoxyphosphoryl)methyl isobutyrate, (dimethoxyphosphoryl)methyl propiolate, (diethoxyphosphoryl)methyl propiolate, (dimethoxyphosphoryl)methyl 3-butynoate, (diethoxyphosphoryl)methyl 3-butynoate, (dimethoxyphosphoryl)methyl methyl carbonate, (diethoxyphosphoryl)methyl methyl carbonate, (dimethoxyphosphoryl)methyl ethyl carbonate, (diethoxyphosphoryl)methyl ethyl carbonate, (dimethoxyphosphoryl)methyl 2-propynyl carbonate, (diethoxyphosphoryl)methyl 2-propynyl carbonate, (dimethoxyphosphoryl)methyl 1-methyl-2-propynyl carbonate, (diethoxyphosphoryl)methyl 1-methyl-2-propynyl carbonate, (dimethoxyphosphoryl)methyl methoxyethyl carbonate, (diethoxyphosphoryl)methyl methoxyethyl carbonate, (dimethoxyphosphoryl)methyl ethoxyethyl carbonate, (diethoxyphosphoryl)methyl ethoxyethyl carbonate, (dimethoxyphosphoryl)methyl methyl oxalate, (diethoxyphosphoryl)methyl methyl oxalate, (dimethoxyphosphoryl)methyl ethyl oxalate, (diethoxyphosphoryl)methyl ethyl oxalate, etc.

(iii) As the case where q is 2:

Preferably mentioned are ethane-1,2-diyl bis(2-(dimethoxyphosphoryl)acetate), ethane-1,2-diyl bis(2-(diethoxyphosphoryl)acetate), propane-1,2-diyl bis(2-(dimethoxyphosphoryl)acetate), propane-1,2-diyl bis(2-(diethoxyphosphoryl)acetate), propane-1,3-diyl bis(2-(dimethoxyphosphoryl)acetate), propane-1,3-diyl bis(2-(diethoxyphosphoryl)acetate), butane-1,4-diyl bis(2-(dimethoxyphosphoryl)acetate), butane-1,4-diyl bis(2-(diethoxyphosphoryl)acetate), butane-2,3-diyl bis(2-(dimethoxyphosphoryl)acetate), butane-2,3-diyl bis(2-(diethoxyphosphoryl)acetate), 2-butyne-1,4-diyl bis(2-(dimethoxyphosphoryl)acetate), 2-butyne-1,4-diyl bis(2-(diethoxyphosphoryl)acetate), 3-hexyne-2,5-diyl bis(2-(diethoxyphosphoryl)acetate), 2,5-dimethyl-3-hexyne-2,5-diyl bis(2-(diethoxyphosphoryl)acetate), bis((dimethoxyphosphoryl)methyl)oxalate, bis((diethoxyphosphoryl)methyl)oxalate, etc.

Of the above-mentioned (i) to (iii), more preferred is one or more selected from 2-propynyl 2-(dimethylphosphoryl)acetate, 2-propynyl 2-(diethylphosphoryl)acetate, 2-propynyl 2-(methoxy(methyl)phosphoryl)acetate, 2-propynyl 2-(ethoxy(ethyl)phosphoryl)acetate, 2-propynyl 2-(dimethoxyphosphoryl)acetate, 2-propynyl 2-(diethoxyphosphoryl)acetate, 2-propynyl 2-(diphenylphosphoryl)acetate, 2-propynyl 2-(diphenoxyphosphoryl)acetate, 2-propynyl 2-(diethoxyphosphoryl)-2-fluracetate, 2-propynyl 2-(dimethoxyphosphoryl)propanoate, 2-propynyl 2-(diethoxyphosphoryl)propanoate, 2-propynyl 3-(dimethoxyphosphoryl)propanoate, 2-propynyl 3-(diethoxyphosphoryl)propanoate, 1-methyl-2-propynyl 2-(diethoxyphosphoryl)acetate, 1,1-dimethyl-2-propynyl 2-(diethoxyphosphoryl)acetate, 2-methoxyethyl 2-(dimethoxyphosphoryl)acetate, 2-methoxyethyl 2-(diethoxyphosphoryl)acetate, 2-trifluoromethylphenyl 2-(dimethoxyphosphoryl)acetate, 3-trifluoromethylphenyl 2-(diethoxyphosphoryl)acetate, 4-trifluoromethylphenyl 2-(dimethoxyphosphoryl)acetate, 4-trifluoromethylphenyl 2-(diethoxyphosphoryl)acetate, methyl 2-(2-oxido-1,3,2-dioxaphospholan-2-yl)acetate, ethyl 2-(2-oxido-1,3,2-dioxaphospholan-2-yl)acetate, 2-propynyl 2-(2-oxido-1,3,2-dioxaphospholan-2-yl)acetate, 2-(2-(diethoxyphosphoryl)acetoxy)ethyl methyl oxalate, 2-(2-(diethoxyphosphoryl)acetoxy)ethyl ethyl oxalate, methyl 2-(2-(diethoxyphosphoryl)acetoxy)propanoate, ethyl 2-(2-(diethoxyphosphoryl)acetoxy)propanoate, (dimethoxyphosphoryl)methyl acetate, (diethoxyphosphoryl)methyl acetate, (dimethoxyphosphoryl)methyl methyl oxalate, (diethoxyphosphoryl)methyl methyl oxalate, ethane-1,2-diyl bis(2-(dimethoxyphosphoryl)acetate), ethane-1,2-diyl bis(2-(diethoxyphosphoryl)acetate), butane-2,3-diyl bis(2-(dimethoxyphosphoryl)acetate), butane-2,3-diyl bis(2-(diethoxyphosphoryl)acetate), 2-butyne-1,4-diyl bis(2-(dimethoxyphosphoryl)acetate), 2-butyne-1,4-diyl bis(2-(diethoxyphosphoryl)acetate), bis((dimethoxyphosphoryl)methyl)oxalate, bis((diethoxyphosphoryl)methyl)oxalate, cyanomethyl 2-(dimethoxyphosphoryl)acetate, cyanomethyl 2-(diethoxyphosphoryl)acetate, 2-cyanoethyl 2-(dimethoxyphosphoryl)acetate, 2-cyanoethyl 2-(diethoxyphosphoryl)acetate, and 1-cyanoethyl 2-(diethoxyphosphoryl)acetate; and even more preferred are 2-propynyl 2-(diethylphosphoryl)acetate, 2-propynyl 2-(ethoxy(ethyl)phosphoryl)acetate, 2-propynyl 2-(dimethoxyphosphoryl)acetate, 2-propynyl 2-(diethoxyphosphoryl)acetate, 2-propynyl 2-(diphenoxyphosphoryl)acetate, 2-propynyl 2-(diethoxyphosphoryl)-2-fluoroacetate, 2-propynyl 3-(diethoxyphosphoryl)propanoate, 1-methyl-2-propynyl 2-(diethoxyphosphoryl)acetate, 1,1-dimethyl-2-propynyl 2-(diethoxyphosphoryl)acetate, 2-methoxyethyl 2-(diethoxyphosphoryl)acetate, 2-trifluoromethylphenyl 2-(diethoxyphosphoryl)acetate, 4-trifluoromethylphenyl 2-(diethoxyphosphoryl)acetate, methyl 2-(2-oxido-1,3,2-dioxaphospholan-2-yl)acetate, 2-propynyl 2-(2-oxido-1,3,2-dioxaphospholan-2-yl)acetate, 2-(2-(diethoxyphosphoryl)acetoxyl)ethyl methyl oxalate, methyl 2-(2-(diethoxyphosphoryl)acetoxyl)propanoate, (diethoxyphosphoryl)methyl acetate, (diethoxyphosphoryl)methyl methyl oxalate, ethane-1,2-diyl bis(2-(diethoxyphosphoryl)acetate), 2-butyne-1,4-diyl bis(2-(diethoxyphosphoryl)acetate), bis((dimethoxyphosphoryl)methyl)oxalate, bis((diethoxyphosphoryl)methyl)oxalate, and 2-cyanoethyl 2-(diethoxyphosphoryl)acetate.

The compounds of which the substituents fall within any of the above-mentioned ranges are preferred, as capable of considerably improving the electrochemical characteristics of energy storage devices at high temperatures.

In the nonaqueous electrolytic solution of the present invention, the content of the organic phosphorus compound represented by the above-mentioned general formula (I) is preferably from 0.001 to 10% by mass of the nonaqueous electrolytic solution. When the content is at most 10% by mass, then the risk of excessive formation of a surface film on the electrode to worsen the high-temperature cycle property of batteries could be low; and when at least 0.001% by mass, then the surface film formation would be sufficient and the effect of improving high-temperature cycle properties could be improved. The content is more preferably at least 0.05% by mass of the nonaqueous electrolytic solution, even more preferably at least 0.2% by mass, and its upper limit is preferably at most 8% by mass, more preferably at most 5% by mass, even more preferably at most 2% by mass.

In the nonaqueous electrolytic solution of the present invention, combining the organic phosphorus compound represented by the above-mentioned general formula (I) with the nonaqueous solvent, electrolyte salt and other additives to be mentioned below exhibits a specific effect of synergistically improving electrochemical characteristics at high temperatures.

[Nonaqueous Solvent]

The nonaqueous solvent for use in the nonaqueous electrolytic solution of the present invention includes cyclic carbonates, linear esters, lactones, ethers, and amides. Preferably, the solvent contains both a cyclic carbonate and a linear ester.

The term "linear ester" is used here as a concept including linear carbonates and linear carboxylates.

As the cyclic carbonates, there may be mentioned at least one selected from ethylene carbonate (EC), propylene carbonate (PC), 1,2-butylene carbonate, 2,3-butylene carbonate, 4-fluoro-1,3-dioxolan-2-one (FEC), trans or cis-4,5-difluoro-1,3-dioxolan-2-one (hereinafter the two are collectively called "DFEC"), vinylene carbonate (VC), and vinylethylene carbonate (VEC).

Of those, preferred is use of at least one cyclic carbonate having a carbon-carbon double bond or a fluorine atom, as markedly improving high-temperature cycle properties; and more preferred is use of both a cyclic carbonate having a carbon-carbon double bond and a cyclic carbonate having a fluorine atom. As the cyclic carbonate having a carbon-carbon double bond, more preferred are VC and VEC; and as the cyclic carbonate having a fluorine atom, more preferred are FEC and DFEC.

The content of the carbon-carbon double bond-containing cyclic carbonate is preferably at least 0.07% by volume relative to the total volume of the nonaqueous solvent, more preferably at least 0.2% by volume, even more preferably at least 0.7% by volume, and the upper limit thereof is preferably at most 7% by volume, more preferably at most 4% by volume, even more preferably at most 2.5% by volume. The range is preferred as capable of markedly improving the stability of surface film during high-temperature cycles.

The content of the fluorine atom-containing cyclic carbonate is preferably at least 0.07% by volume relative to the total volume of the nonaqueous solvent, more preferably at least 4% by volume, even more preferably at least 7% by volume, and the upper limit thereof is preferably at most 35% by volume, more preferably at most 25% by volume, even more preferably at most 15% by volume. The range is preferred as capable of markedly improving the stability of surface film during high-temperature cycles.

In case where the nonaqueous solvent contains both a carbon-carbon double bond-containing cyclic carbonate and a fluorine atom-containing cyclic carbonate, the content of the carbon-carbon double bond-containing cyclic carbonate relative to the content of the fluorine atom-containing cyclic carbonate is preferably at least 0.2% by volume, more preferably at least 3% by volume, even more preferably at least 7% by volume, and its upper limit is preferably at most 40% by volume, more preferably at most 30% by volume, even more preferably at most 15% by volume. The range is preferred as capable of markedly improving the stability of surface film during high-temperature cycles.

Preferably, the nonaqueous solvent contains ethylene carbonate and/or propylene carbonate, as the resistance of the surface film formed on electrodes can be reduced. Preferably, the content of ethylene carbonate and/or propylene carbonate is at least 3% by volume relative to the total volume of the nonaqueous solvent, more preferably at least 5% by volume, even more preferably at least 7% by volume, and its upper limit is preferably at most 45% by volume, more preferably at most 35% by volume, even more preferably at most 25% by volume.

One kind of those solvents may be used, but using two or more different kinds thereof as combined is preferred as further improving electrochemical characteristics at high temperatures. Even more preferably, three or more different kinds are combined. Preferred combinations of the cyclic carbonates include EC and PC; EC and VC; PC and VC; VC and EEC; EC and EEC; PC and EEC; FEC and DEEC; EC and DEEC; PC and DEEC; VC and DFEC; VEC and DEEC; EC and PC and VC; EC and PC and EEC; EC and VC and EEC; EC and VC and VEC; PC and VC and FEC; EC and VC and DFEC; PC and VC and DEEC; EC and PC and VC and EEC; EC and PC and VC and DEEC; etc. Of those combinations, more preferred combinations are EC and VC; EC and EEC; PC and FEC; EC and PC and VC; EC and PC and FEC; EC and VC and EEC; PC and VC and EEC; EC and PC and VC and FEC; etc.

As the linear esters, preferably mentioned are asymmetric linear carbonates, such as methyl ethyl carbonate (MEC), methyl propyl carbonate (MPC), methyl isopropyl carbonate (MIPC), methyl butyl carbonate, and ethyl propyl carbonate, etc.; symmetric linear carbonates, such as dimethyl carbonate (DMC), diethyl carbonate (DEC), dipropyl carbonate, dibutyl carbonate, etc.; pivalates, such as methyl pivalate, ethyl pivalate, propyl pivalate, etc.; linear carboxylates, such as methyl propionate, ethyl propionate, methyl acetate, ethyl acetate, etc.

Of the above-mentioned linear esters, preferred are methyl group-having linear esters selected from dimethyl carbonate, methyl ethyl carbonate, methyl propyl carbonate, methyl isopropyl carbonate, methyl butyl carbonate, methyl propionate, methyl acetate and ethyl acetate; and more preferred are methyl group-having linear carbonates.

Preferably, two or more different types of linear carbonates are used here. More preferably, a combination of a symmetric linear carbonate and an asymmetric linear carbonate is used; and even more preferably, the content of the symmetric linear carbonate is larger than that of the asymmetric linear carbonate.

Not specifically defined, the content of the linear ester is preferably within a range of from 60 to 90% by volume relative to the total volume of the nonaqueous solvent. When the content is at least 60% by volume, then the viscosity of the nonaqueous electrolytic solution would not be too high; and when at most 90% by volume, then the risk of lowering the electric conductivity of the nonaqueous electrolytic solution to worsen electrochemical characteristics at high temperatures may be low. For these reasons, the above-mentioned range is preferred here.

Preferably, two or more different types of linear carbonates are used here. More preferably, a combination of a symmetric linear carbonate and an asymmetric linear carbonate is used; and even more preferably, the content of the symmetric linear carbonate is larger than that of the asymmetric linear carbonate.

The ratio by volume of the symmetric linear carbonate to the linear carbonate is preferably at least 51% by volume, more preferably at least 55% by volume, and its upper limit is preferably at most 95% by volume, more preferably at most 85% by volume. Especially preferably, the symmetric linear carbonate for use herein contains dimethyl carbonate. Also preferably, the asymmetric linear carbonate for use herein has a methyl group, and especially preferred is use of methyl ethyl carbonate here.

The above-mentioned embodiments are preferred as improving electrochemical characteristics at high temperatures.

The ratio of the cyclic carbonate to the linear ester, cyclic carbonate/linear ester (by volume) is preferably from 10/90 to 45/55, more preferably from 15/85 to 40/60, even more preferably from 20/80 to 35/65, from the viewpoint of improving electrochemical characteristics at high temperatures.

As other nonaqueous solvents preferred for use herein, there are mentioned cyclic ethers, such as tetrahydrofuran, 2-methyltetrahydrofuran, 1,3-dioxolane, 1,3-dioxane, 1,4-dioxane, etc.; linear ethers, such as 1,2-dimethoxyethane, 1,2-diethoxyethane, 1,2-dibutoxyethane, etc.; amides, such as dimethylformamide, etc.; sulfones, such as sulfolane, etc.; lactones, such as γ-butyrolactone, γ-valerolactone, α-angelicalactone, etc.

For the purpose of markedly improving electrochemical characteristics at high temperatures, it is desirable that any other additive is further added to the nonaqueous electrolytic solution.

As preferred examples of the other additives, further mentioned are phosphorus-containing compounds, such as trimethyl phosphate, tributyl phosphate, trioctyl phosphate, methyl methylenebisphosphonate, ethyl methylenebisphosphonate, methyl ethylenebisphosphonate, ethyl ethylenebisphosphonate, methyl butylenebisphosphonate, ethyl butylenebisphosphonate, methyl dimethylphosphonoacetate, ethyl dimethylphosphonoacetate, methyl diethylphosphonoacetate, ethyl diethylphosphonoacetate, methyl pyrophosphate, ethyl pyrophosphate, etc.; benzene compounds with an aliphatic hydrocarbon group having from 1 to 6 carbon atoms and bonding to the benzene ring via a tertiary carbon atom or a quaternary carbon atom, such as cyclohexylbenzene, fluorocyclohexylbenzene (1-fluoro-2-cyclohexylbenzene, 1-fluoro-3-cyclohexylbenzene, 1-fluoro-4-cyclohexylbenzene), tert-butylbenzene, 1,3-di-tert-butylbenzene, tert-amylbenzene, 1-fluoro-4-tert-butylbenzene, etc.; oxalates, such as dimethyl oxalate, ethylmethyl oxalate, diethyl oxalate, etc.; nitriles, such as acetonitrile, propionitrile, succinonitrile, glutaronitrile, adiponitrile, pimelonitrile, etc.; isocyanates, such as tetramethylene diisocyanate, hexamethylene diisocyanate, octamethylene diisocyanate, etc.; triple bond-having compounds such as 2-propynylmethyl carbonate, 2-propynyl acetate, 2-propynyl formate, 2-propynyl methacrylate, 2-propynyl methanesulfonate, di(2-propynyl) oxalate, di(2-propynyl)glutarate, 2-butyne-1,4-diyl dimethanesulfonate, 2-butyne-1,4-diyl diformate, 2,4-hexadiyne-1,6-diyl dimethanesulfonate, etc.; S=O group-containing compounds selected from sultones, such as 1,3-propanesultone, 1,3-butanesultone, 1,4-butanesultone, etc., cyclic sulfites, such as ethylene sulfite, hexahydrobenzo[1,3,2]dioxathiol-2-oxide (also referred to as 1,2-cyclohexanediol cyclic sulfite), 5-vinyl-hexahydrobenzo[1,3,2]dioxathiol-2-oxide, 4-(methylsulfonylmethyl)-1,3,2-dioxathiolane-2-oxide, etc., sulfonates such as butane-1,4-diyl dimethanesulfonate, pentane-1,5-diyl dimethanesulfonate, propane-1,2-diyl dimethanesulfonate, butane-2,3-diyl dimethanesulfonate, dimethylmethylene disulfonate, methylenemethane disulfonate, 2-trifluoromethylphenyl methanesulfonate, pentafluorophenyl methanesulfonate, etc., and vinyl sulfones, such as divinyl sulfone, 1,2-bis(vinylsulfonyl)ethane, bis(2-vinylsulfonylethyl)ether, etc.; phosphoric acid anhydrides, such as tetramethyldiphosphonic acid anhydride, tetraethyldiphosphonic acid anhydride, etc.; linear carboxylic acid anhydrides, such as acetic anhydride, propionic anhydride, etc.; cyclic acid anhydrides such as succinic anhydride, maleic anhydride, glutaric anhydride, itaconic anhydride, 3-sulfo-propionic acid anhydride, etc.; cyclic phosphazenes, such as methoxypentafluorocyclotriphosphazene, ethoxypentafluorocyclotriphosphazene, phenoxypentafluorocyclotriphosphazene, ethoxypentafluorocyclotetraphosphazene, etc.; aromatic compounds, such as partial hydrides of biphenyl, terphenyl (o-, m-, p-form), diphenyl ether, fluorobenzene, difluorobenzene (o-, m-, p-form), anisole, 2,4-difluoroanisole or terphenyl(1,2-dicyclohexylbenzene, 2-phenylbicyclohexyl, 1,2-diphenylcyclohexane, o-cyclohexylbiphenyl), etc.

Of the above, more preferred are nitriles and/or aromatic compounds, since the nonaqueous electrolytic solution containing any of them can markedly improve battery characteristics at high temperatures. Of nitriles, more preferred is at least one selected from succinonitrile, glutaronitrile, adiponitrile and pimelonitrile. Of aromatic compounds, more preferred are biphenyl, cyclohexylbenzene, tert-butylbenzene, and tert-amylbenzene. The content of nitrile and/or aromatic compound in the nonaqueous electrolytic solution is preferably from 0.001 to 5% by mass. When the content is more than 0.001% by mass, then the surface film formation would be sufficient and the effect of improving high-temperature cycle properties could be thereby improved. The content is more preferably at least 0.005% by mass in the nonaqueous electrolytic solution, even more preferably at least 0.01% by mass, still more preferably at least 0.03% by mass, and its upper limit is preferably at most 3% by mass, more preferably at most 1% by mass, even more preferably at most 0.4% by mass.

Also preferably, the nonaqueous electrolytic solution contains any of (a) a triple bond-having compound, (b) a cyclic or linear S=O group-having compound selected from sultones, cyclic sulfites, sulfonates, and vinyl sulfones, or (c) a phosphorus-containing compound, as capable of markedly improving electrochemical characteristics at high temperatures.

As the triple bond-having compound (a), preferred is 2-propynyl methyl carbonate, 2-propynyl methacrylate, 2-propynyl methanesulfonate, di(2-propynyl)oxalate, or 2-butyne-1,4-diyl dimethanesulfonate; and more preferred is at least one selected from 2-propynyl methanesulfonate, di(2-propynyl)oxalate, and 2-butyne-1,4-diyl dimethanesulfonate.

The content of the triple bond-having compound in the nonaqueous electrolytic solution is preferably from 0.001 to 5% by mass. When the content is more than 0.001% by mass, then the surface film formation would be sufficient and the effect of improving high-temperature cycle properties could be thereby improved. The content is more preferably at least 0.005% by mass in the nonaqueous electrolytic solution, even more preferably at least 0.01% by mass, still more preferably at least 0.03% by mass, and its upper limit is preferably at most 3% by mass, more preferably at most 1% by mass, even more preferably at most 0.7% by mass.

As the cyclic S=O group-having compound (but not containing a triple bond) (b), preferred is at least one selected from 1,3-propanesultone, 1,3-butanesultone, 1,4-butanesultone, 2,4-butanesultone, methylene methanedisulfonate, ethylene sulfite, and 4-(methylsulfonylmethyl)-1,3,2-dioxathiolane-2-oxide; and more preferred is at least one selected from 1,3-propanesultone, 1,4-butanesultone, and 2,4-butanesultone.

As the linear S=O group-having compound, preferred is butane-2,3-diyl dimethanesulfonate, butane-1,4-diyl dimethanesulfonate, dimethyl methanedisulfonate, 2-trifluoromethylphenyl methanesulfonate, pentafluorophenyl methanesulfonate, divinyl sulfone, or bis(2-vinylsulfonylethyl) ether; more preferred is at least one sulfonate selected from butane-2,3-diyl dimethanesulfonate, butane-1,4-diyl dimethanesulfonate, dimethyl methanedisulfonate, 2-trifluoromethylphenyl methanesulfonate, and pentafluorophenyl methanesulfonate; and even more preferred is at least one selected from butane-2,3-diyl dimethanesulfonate, and pentafluorophenyl methanesulfonate.

The content of the S=O group-having compound in the nonaqueous electrolytic solution is preferably from 0.001 to 5% by mass. When the content is more than 0.001% by mass, then the surface film formation would be sufficient and the effect of improving high-temperature cycle properties could be thereby improved. The content is more preferably at least 0.005% by mass in the nonaqueous electrolytic solution, even more preferably at least 0.01% by mass, still more preferably at least 0.03% by mass, and its upper limit is preferably at most 3% by mass, more preferably at most 1% by mass, even more preferably at most 0.7% by mass.

As the phosphorus-containing compound (c), more preferred is at least one selected from trimethyl phosphate, methyl methylenebisphosphonate, ethyl methylenebisphosphonate, methyl diethylphosphonoacetate, ethyl diethylphosphonoacetate, and ethyl pyrophosphate; and even more preferred is at least one selected from ethyl methylenebisphosphonate, ethyl diethylphosphonoacetate and ethyl pyrophosphate.

The content of the phosphorus-containing compound in the nonaqueous electrolytic solution is preferably from 0.001 to 5% by mass. When the content is more than 0.001% by mass, then the surface film formation would be sufficient and the effect of improving high-temperature cycle properties could be thereby improved. The content is more preferably at least 0.005% by mass in the nonaqueous electrolytic solution, even more preferably at least 0.01% by mass, still more preferably at least 0.03% by mass, and its upper limit is preferably at most 3% by mass, more preferably at most 1% by mass, even more preferably at most 0.7% by mass, and especially preferably at most 0.4% by mass.

[Electrolyte Salt]

As the electrolyte salt for use in the present invention, preferably mentioned are the following lithium salts and onium salts.

(Lithium Salt)

The lithium salt includes inorganic lithium salts, such as $LiPF_6$, $LiPO_2F_2$, $Li_2PO_3F$, $LiBF_4$, $LiClO_4$, $LiSO_3F$, etc.; linear fluoroalkyl group-having lithium salts, such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic fluoroalkylene chain-having lithium salts, such as $(CF_2)_2(SO_2)_2NLi$, $(CF_2)_3(SO_2)_2NLi$, etc.; and lithium salts with an oxalate complex as the anion therein, such as lithium bis[oxalate-O,O']borate, lithium difluoro[oxalate-O,O']borate, lithium difluorobis[oxalate-O,O']phosphate, lithium tetrafluoro[oxalate-O,O'] phosphate, etc. One or more of these as combined may be used here. Of those, preferred is at least one selected from $LiPF_6$, $LiPO_2F_2$, $Li_2PO_3F$, $LiBF_4$, $LiSO_3F$, $LiN(SO_2CF_3)_2$ and $LiN(SO_2C_2F_5)_2$, $LiN(SO_2F)_2$, lithium difluorobis[oxalate-O,O']phosphate and lithium tetrafluoro[oxalate-O,O'] phosphate; and more preferred is at least one selected from $LiPF_6$, $LiPO_2F_2$, $LiBF_4$, $LiN(SO_2CF_3)_2$, $LiN(SO_2F)_2$, and lithium difluorobis[oxalate-O,O']phosphate. The concentration of the lithium salt is, in general, preferably at least 0.3 M relative to the above-mentioned nonaqueous solvent, more preferably at least 0.7 M, even more preferably at least 1.1 M. The upper limit of the content is preferably at most 2.5 M, more preferably at most 2.0 M, even more preferably at most 1.6 M.

A preferred combination of these lithium salts to be contained in the nonaqueous electrolytic solution comprises $LiPF_6$ and contains at least one lithium salt selected from $LiPO_2F_2$, $LiBF_4$, $LiN(SO_2CF_3)_2$, $LiN(SO_2F)_2$ and lithium difluorobis[oxalate-O,O']phosphate. The proportion of the lithium salt except $LiPF_6$ in the nonaqueous solvent is preferably at least 0.001 M, as readily exhibiting the effect of improving electrochemical characteristics at high temperatures, and is also preferably at most 0.005 M as free from the risk of lowering the effect of improving electrochemical characteristics at high temperatures. More preferably, the proportion is at least 0.01 M, even more preferably at least 0.03 M, and most preferably at least 0.04 M. The upper limit of the proportion is preferably at most 0.4 M, more preferably at most 0.2 M.

(Onium Salt)

Preferred examples of the onium salt are various salts of a combination of an onium cation and an anion mentioned below.

As specific examples of the onium cation, preferably mentioned are a tetramethylammonium cation, an ethyltrimethylammonium cation, a diethyldimethylammonium cation, a triethylmethylammonium cation, a tetraethylammonium cation, an N,N-dimethylpyrrolidinium cation, an N-ethyl-N-methylpyrrolidinium cation, an N,N-diethylpyrrolidinium cation, a Spiro-(N,N')-bipyrrolidinium cation, an N,N'-dimethylimidazolinium cation, an N-ethyl-N'-methylimidazolinium cation, an N,N'-diethylimidazolinium cation, an N,N'-dimethylimidazolinium cation, an N-ethyl-N'-methylimidazolinium cation, an N,N'-diethylimidazolinium cation, etc.

Preferred examples of the anion include a $PF_6$ anion, a $BF_4$ anion, a $ClO_4$ anion, an $AsF_6$ anion, a $CF_3SO_3$ anion, an $N(CF_3SO_2)_2$ anion, an $N(C_2F_5SO_2)_2$ anion, etc.

One alone or two or more different types of these onium salts may be used here either singly or as combined.

[Production of Nonaqueous Electrolytic Solution]

The nonaqueous electrolytic solution of the present invention may be produced, for example, by mixing the above-mentioned nonaqueous solvents, adding the above-mentioned electrolyte salt, and further adding thereto the organic phosphorus compound represented by the above-mentioned general formula (I) to the resulting nonaqueous electrolytic solution.

Preferably, the nonaqueous solvent to be used and the compound to be added to the nonaqueous electrolytic solution are previously purified to reduce as much as possible the content of impurities therein within a range not extremely detracting from the productivity.

The nonaqueous electrolytic solution of the present invention can be used in the first to fourth energy storage devices mentioned below, in which as the nonaqueous electrolyte, not only a liquid one but also a gelled one may be used. Further, the nonaqueous electrolytic solution of the present invention can also be used for solid polymer electrolytes. Especially preferably, the solution is used in the first energy storage device where a lithium salt is used as the electrolyte salt (that is, for lithium batteries), or in the fourth energy storage device (that is, for lithium ion capacitors); and more suitably, the solution is used for lithium batteries, even more preferably for lithium secondary batteries.

[First Energy Storage Device (Lithium Battery)]

The lithium battery in this specification means a generic name for a lithium primary battery and a lithium secondary battery. In this specification, the term, lithium secondary battery is used as a concept that includes so-called lithium ion secondary batteries. The lithium battery of the present invention comprises a positive electrode, a negative electrode, and the above-mentioned nonaqueous electrolytic solution of an electrolyte salt dissolved in a nonaqueous solvent. The other constitutive members, such as the positive electrode, the negative electrode and others than the nonaqueous electrolytic solution are not specifically defined for use herein.

For example, as the positive electrode active material for lithium secondary batteries, usable is a complex metal oxide of lithium and one or more selected from cobalt, manganese and nickel. One alone or two or more of these positive electrode active materials may be used here either singly or as combined.

The lithium complex metal oxide includes, for example, $LiCoO_2$, $LiMn_2O_4$, $LiNiO_2$, $LiCo_{1-x}Ni_xO_2$ (0.01<x<1), $LiCo_{1/3}Ni_{1/3}Mn_{1/3}O_2$, $LiNi_{1/2}Mn_{3/2}O_4$, $LiCo_{0.98}Mg_{0.02}O_2$, etc. Also usable here is a combination of $LiCoO_2$ and $LiMn_2O_4$, a combination of $LiCoO_2$ and $LiNiO_2$, or a combination of $LiMn_2O_4$ and $LiNiO_2$.

For improving the safety in overcharging and the cycle properties of the batteries, or for enabling the use thereof at a charge potential of 4.3 V or more, a part of the lithium complex metal oxide may be substituted with any other element. For example, a part of cobalt, manganese and nickel may be substituted with at least one or more elements of Sn, Mg, Fe, Ti, Al, Zr, Cr, V, Ga, Zn, Cu, Bi, Mo, La, etc.; or a part of O may be substituted with S or F; or the oxide may be coated with a compound containing any of such other elements.

Of those, preferred are lithium complex metal oxides, such as $LiCoO_2$, $LiMn_2O_4$ and $LiNiO_2$, with which the charge potential of the positive electrode in a fully-charged state could be 4.3 V or more based on Li; and more preferred are lithium complex metal oxides, such as solid solutions of $LiCo_{1-x}M_xO_2$ (where M is one or more elements selected from Sn, Mg, Fe, Ti, Al, Zr, Cr, V, Ga, Zn and Cu; $0.001 \leq x \leq 0.05$), $LiCo_{1/3}Ni_{1/3}Mn_{1/3}O_2$, $LiNi_{1/2}Mn_{3/2}O_4$, $Li_2MnO_3$ and $LiMO_2$ (where M is a transition metal, such as Co, Ni, Mn, Fe, etc.) that can be used at 4.4 V or more. When the lithium complex metal oxide capable of acting at a high charge voltage is used, then the electrochemical characteristics at high temperatures may often worsen owing to the reaction of the oxide with the electrolytic solution in charging; however, in the lithium secondary battery of the present invention, the electrochemical characteristics can be prevented from worsening.

The pH of the supernatant prepared by dispersing 10 g of the above-mentioned positive electrode active material in 100 ml of distilled water is preferably from 10.0 to 12.5 as the effect of improving high-temperature cycle properties can be further markedly augmented, and is more preferably from 10.5 to 12.0.

In case where an element Ni is contained in the positive electrode, impurities, such as LiOH in the positive electrode active material may increase and the case is therefore preferred as the effect of improving high-temperature cycle properties can also be markedly augmented. More preferably, the atomic concentration of Ni in the positive electrode active material is from 5 to 25 atomic %, even more preferably from 8 to 21 atomic %.

Further, as the positive electrode active material, also usable are lithium-containing olivine-type phosphates. Especially preferred are lithium-containing olivine-type phosphates containing at least one selected from iron, cobalt, nickel and manganese. Specific examples thereof include $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel, and manganese therein may be substituted with at least one element selected from Co, Mn, Ni, Mg, Al, B, Ti, V, Nb, Cu, Zn, Mo, Ca, Sr, W, and Zr; or the phosphates may be coated with a compound containing any of these other elements or with a carbon material. Among these, preferred are $LiFePO_4$ and $LiMnPO_4$.

Further, the lithium-containing olivine-type phosphate may be combined with, for example, the above-mentioned positive electrode active materials.

For the positive electrode for lithium primary batteries, there are mentioned oxides or chalcogen compounds of one or more metal elements, such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds, such as $SO_2$, $SOCl_2$, etc.; carbon fluorides (graphite fluoride) represented by a general formula $(CF_x)_n$, etc. Of those, preferred are $MnO_2$, $V_2O_5$, fluorographite, etc.

Not specifically defined, the electroconductive agent of the positive electrode may be any electron-conductive material not undergoing chemical change. For example, it includes graphites, such as natural graphite (flaky graphite, etc.), artificial graphite, etc.; carbon blacks, such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent, such as acetylene black, carbon black or the like, and with a binder, such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent, such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 g/cm$^3$, and for further increasing the capacity of the battery, the density is preferably at least 2 g/cm$^3$, more preferably at least 3 g/cm$^3$, even more preferably at least 3.6 g/cm$^3$. The upper limit is preferably at most 4 g/cm$^3$.

As the negative electrode active material for lithium secondary batteries, usable are one or more of lithium metal, lithium alloys, carbon materials capable of absorbing and releasing lithium [graphatizable carbon, non-graphatizable carbon where the lattice (002) spacing is at least 0.37 nm, graphite where the lattice (002) spacing is at most 0.34 nm, etc.], tin (elementary substance), tin compounds, silicon (elementary substance), silicon compounds, lithium titanate compounds, such as $Li_4Ti_5O_{12}$ and the like, either singly or as combined with two or more thereof.

Of those, more preferred is use of high-crystalline carbon materials, such as artificial graphite, natural graphite and the like, in view of the ability thereof to absorb and release lithium ions, and even more preferred is use of a carbon material having a graphite-type crystal structure where the lattice (002) spacing ($d_{002}$) is at most 0.340 nm (nanometers), especially from 0.335 to 0.337 nm.

In particular, preferred here is use of artificial graphite particles having a bulky structure where plural flattened graphite fine particles aggregate or bond together non-parallel to each other, or graphite particles produced through treatment of spheroidization of flaky natural graphite particles by imparting thereto repeated mechanical action, such as compression force, friction force, shear force or the like. Preferably, the ratio of the peak intensity I(110) of the (110) plane of the graphite crystal obtained in X-ray diffractiometry of a negative electrode sheet as formed by pressing so that the density of the part except the collector of the negative electrode could be at least 1.5 g/cm$^3$, to the peak intensity I(004) of the (004) plane thereof, I(110)/I(004) is at least 0.01, since the electrochemical characteristics at high temperatures of the battery can be markedly improved. More preferably, the ratio is at least 0.05, even more preferably at least 0.1. On the other hand, when too much processed, then the crystallinity may worsen and the discharge capacity of the battery may lower; and therefore, the upper limit of the peak intensity I(110)/I(004) is preferably at most 0.5, more preferably at most 0.3.

Preferably, the high-crystalline carbon material (core material) is coated with a different carbon material that is more low-crystalline than the core material, as further bettering electrochemical characteristics at high temperatures. The crystallinity of the carbon material in coating may be confirmed through TEM.

When the high-crystalline carbon material is used, it may readily react with the nonaqueous electrolytic solution in charging to thereby worsen electrochemical characteristics at high temperatures owing to the increase in the interfacial resistance; however, in the lithium secondary battery of the present invention, the electrochemical characteristics at high temperatures can be bettered.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of elementary substances, alloys, oxides, nitrides, sulfides, borides, alloys with lithium or the like; but preferred are any of elementary substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the battery capacity.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

The density of the part except the collector of the negative electrode may be generally at least 1.1 g/cm$^3$, and for further increasing the battery capacity, the density is preferably at least 1.5 g/cm$^3$, more preferably at least 1.7 g/cm$^3$. The upper limit is preferably at most 2 g/cm$^3$.

As the negative electrode active material for lithium primary batteries, usable are lithium metal or lithium alloys.

The structure of the lithium battery is not specifically defined. The battery may be a coin-type battery, a cylinder-type battery, a square-shaped battery, a laminate-type battery or the like, each having a single-layered or multi-layered separator.

The separator for the battery is not specifically defined, for which usable is a single-layer or laminate porous film of polyolefin, such as polypropylene, polyethylene or the like, as well as a woven fabric, a nonwoven fabric, etc.

The lithium secondary battery of the present invention has excellent electrochemical characteristics at high temperatures even when the final charging voltage is 4.2 V or more, especially 4.3 V or more, and further, the electrochemical characteristics of the battery are still good even at 4.4 V or more. The final discharging voltage could be generally 2.8 V or more, further 2.5 V or more; however, the final discharging voltage of the lithium secondary battery of the present invention could be 2.0 V or more. The current value is not specifically defined, but in general, the battery is used within a range of from 0.1 to 30 C. The lithium battery of the present invention can be charged/discharged at −40 to 100° C., preferably at −10 to 80° C.

In the present invention, as a countermeasure against the increase in the internal pressure of the lithium battery, there may be employed a method of providing a safety valve in the battery cap or a method of forming a cutout in the battery component, such as the battery can, the gasket or the like. In addition, as a safety countermeasure against overcharging, a current cut-off mechanism capable of detecting the internal pressure of the battery to cut off the current may be provided in the battery cap.

[Second Energy Storage Device (Electric Double-Layer Capacitor)]

This is an energy storage device that stores energy by utilizing the electric double layer capacitance in the interface between the electrolytic solution and the electrode therein. One example of the present invention is an electric double layer capacitor. The most typical electrode active material to be used in the energy storage device is active carbon. The double layer capacitance increases almost in proportion to the surface area.

[Third Energy Storage Device]

This is an energy storage device that stores energy by utilizing the doping/dedoping reaction of the electrode therein. As the electrode active material for use in the energy storage device, there may be mentioned metal oxides, such as ruthenium oxide, iridium oxide, tungsten oxide, molybdenum oxide, copper oxide, etc.; π-conjugated polymers, such as polyacene, polythiophene derivatives, etc. The capacitor that uses the electrode active material of the type enables energy storage along with the doping/dedoping reaction at the electrode therein.

[Fourth Energy Storage Device (Lithium Ion Capacitor)]

This is an energy storage device that stores energy by utilizing the lithium ion intercalation into the carbon material, such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the π-conjugated polymer electrode therein. The electrolytic solution contains at least a lithium salt, such as $LiPF_6$ or the like.

[Organic Phosphorus Compound]

The organic phosphorus compound of the present invention, which is a novel compound, is represented by the following general formula (II):

[Chem. 4]

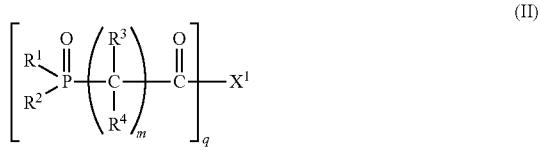

(II)

(In the formula, $R^1$ and $R^2$ each independently represent an alkyl group having from 1 to 6 carbon atoms, a cycloalkyl group having from 3 to 6 carbon atoms, an alkenyl group having from 2 to 6 carbon atoms, an alkynyl group having from 3 to 6 carbon atoms, an alkoxy group having from 1 to 6 carbon atoms, a cycloalkoxy group having from 3 to 6 carbon atoms, an alkenyloxy group having from 2 to 6 carbon atoms, an alkynyloxy group having from 3 to 6 carbon atoms, a halogenoalkyl group having from 1 to 6 carbon atoms, a halogenoalkoxy group having from 1 to 6 carbon atoms, an aryl group having from 6 to 12 carbon atoms in which at least one hydrogen atom may be substituted with a halogen atom, or an aryloxy group having from 6 to 12 carbon atoms in which at least one hydrogen atom may be substituted with a halogen atom, and in a case where $R^1$ and $R^2$ each are an alkyl group or an alkoxy group, $R^1$ and $R^2$ may bond to form a cyclic structure.

$R^3$ and $R^4$ each independently represent a hydrogen atom, a halogen atom, or an alkyl group having from 1 to 4 carbon atoms; m indicates an integer of from 1 to 4; and q indicates 1 or 2. In case where q is 1, $X^1$ represents an alkynyloxy group having from 3 to 6 carbon atoms, an aryloxy group having from 7 to 12 carbon atoms in which at least one hydrogen atom on the benzene ring is substituted with a trifluoromethyl group, —O-$L^1$-OC(=O)—C(=O)—$OR^5$, —O-$L^2$-C(=O)—$OR^5$, or —O-$L^5$-CN; in case where q is 2, $X^1$ represents —O-$L^4$-O—, or —OC(=O)—C(=O)O—. Further, $R^5$ represents an alkyl group having from 1 to 6 carbon atoms; $L^1$ represents an alkylene group having from 2 to 6 carbon atoms, or an alkynylene group having from 4 to 8 carbon atoms; $L^2$ and $L^5$ each represent an alkylene group having from 1 to 6 carbon atoms; and $L^4$ represents an alkynylene group having from 4 to 8 carbon atoms.)

In the general formula (II), the alkynylene group having from 4 to 8 carbon atoms for the substituent $L^4$ has already been described in the section of the above-mentioned general formula (I), and is therefore omitted in this section for avoiding duplication. In the case, the substituent $L^3$ in the general formula (I) shall be read as the substituent $L^4$ in the general formula (II).

The substituents $R^1$, $R^2$, $R^3$, $R^4$, $L^1$, $L^2$ and $L^5$ in the general formula (II) have the same meanings as in the general formula (I).

The organic phosphorus compound of the present invention can be produced according to the following methods (a) to (c), to which, however, the compound production is not limited.

(a) A method of reacting an organic phosphorus-carboxylic acid halide with a corresponding hydroxy compound through esterification in or not in a solvent and in the presence or absence of a base (hereinafter this may be referred to as "method (a)").

(b) A method of reacting an organic phosphorus-carboxylic acid with a corresponding hydroxy compound through condensation in or not in a solvent and in the presence of an acid catalyst or a dehydrating agent (hereinafter this may be referred to as "method (b)").

(c) A method of reacting an organic phosphorus-carboxylic acid ester with a corresponding hydroxy compound through transesterification in or not in a solvent and in the presence of a catalyst (hereinafter this may be referred to as "method (c)").

[Method (a)]

The method (a) comprises reacting an organic phosphorus-carboxylic acid halide with a corresponding hydroxy compound through esterification in or not in a solvent and in the presence or absence of a base. The starting material, organic phosphorus-carboxylic acid halide can be synthesized according to an already-existing ordinary method. For example, the halide can be synthesized according to a method of reacting an organic phosphorus-carboxylic acid with thionyl chloride as described in Organic Letters, 6, (20), p. 3477 (2004).

In the reaction of the method (a), the amount of the hydroxy compound to be used is preferably from 0.8 to 20 mols relative to 1 mol of the organic phosphorus-carboxylic acid halide therein, more preferably from 0.9 to 10 mols, even more preferably from 1 to 5 mols.

The hydroxy compound to be used in the method (a) includes 2-propyn-1-ol, 2-butyn-1-ol, 3-butyl-1-ol, 4-pentyn-1-ol, 5-hexyne-1-ol, 2-methyl-2-propyn-1-ol, 2,2-dimethyl-2-propyn-1-ol, 2-butyne-1,4-diol, 3-hexyne-2,5-diol, 2,5-dimethyl-3-hexyne-2,5-diol, 2-trifluoromethylphenol, 3-trifluoromethylphenol, 4-trifluoromethylphenol, 2,4-bis (trifluoromethyl)phenol, 3,5-bis(trifluoromethyl)phenol, etc.

The reaction of the method (a) may advance in the absence of a solvent, for which, however, a solvent inert to the reaction may be used. The solvent to be used includes aliphatic hydrocarbons, such as heptane, cyclohexane, etc.; halogenohydrocarbons, such as dichloromethane, dichloroethane, etc.; aromatic hydrocarbons, such as toluene, xylene, etc.; halogenoaromatic hydrocarbons, such as chlorobenzene, fluorobenzene, etc.; ethers, such as diisopropyl ether, dioxane, dimethoxyethane, etc.; esters, such as ethyl acetate, butyl acetate, dimethyl carbonate, diethyl carbonate, etc.; nitriles, such as acetonitrile, propionitrile, etc.; sulfoxides, such as dimethyl sulfoxide, sulfolane, etc.; amides, such as N,N- dimethylformamide, N,N-dimethylacetamide, etc.; or and their mixtures. Of those, preferred are aliphatic or aromatic hydrocarbons and esters, such as heptane, cyclohexane, toluene, ethyl acetate, dimethyl carbonate, etc.

The amount of the solvent to be used is preferably from 0 to 30 parts by mass relative to 1 part by mass of the organic phosphorus-carboxylic acid halide, more preferably from 1 to 10 parts by mass.

The reaction of the method (a) may advance in the absence of a base, for which, however, the presence of a base is preferred as promoting the reaction. As the base, any of an inorganic base or an organic base is employable here.

The inorganic base includes potassium carbonate, sodium carbonate, calcium hydroxide and calcium oxide. The organic base includes linear or branched aliphatic tertiary amines, and unsubstituted or substituted imidazoles, pyridines and pyrimidines. Of those, preferred are trialkylamines, such as trimethylamine, triethylamine, tripropylamine, tributylamine, diisopropylethylamine, etc.; and pyridines, such as pyridine, N,N-dimethylaminopyridine, etc.

The amount of the base to be used is preferably from 0.8 to 5 mols relative to 1 mol of the organic phosphorus-carboxylic acid halide, more preferably from 1 to 3 mols, even more preferably from 1 to 1.5 mols.

In the reaction of the method (a), the lower limit of the reaction temperature is preferably not lower than $-20°$ C. from the viewpoint of not lowering the reactivity, and is more preferably not lower than $-10°$ C. Also from the viewpoint of preventing any side reaction and product decomposition, the upper limit of the reaction temperature is preferably not higher than 100° C., and is more preferably not higher than 80° C.

The reaction time may be varied suitably, depending on the reaction temperature and the reaction scale; however, when the reaction time is too short, then unreacted matters may remain, but on the contrary, when the reaction time is too long, then the reaction product would be decomposed and some side reaction would occur. Therefore, the reaction time is preferably from 0.1 to 12 hours, more preferably from 0.2 to 6 hours.

[Method (b)]

The method (b) comprises reacting an organic phosphorus-carboxylic acid with a corresponding hydroxy compound through condensation in or not in a solvent and in the presence of an acid catalyst or a dehydrating agent.

In the reaction of the method (b), the amount of the hydroxy compound to be used is preferably from 0.8 to 20 mols relative to 1 mol of the organic phosphorus-carboxylic acid therein, more preferably from 0.9 to 10 mols, even more preferably from 1 to 5 mols.

The hydroxy compound to be used in the method (b) includes those described in the section of the method (a).

The reaction of the method (b) may advance in the absence of a solvent, for which, however, a solvent inert to the reaction may be used. The solvent to be used includes aliphatic hydrocarbons, halogenohydrocarbons, aromatic hydrocarbons, halogenoaromatic hydrocarbons, ethers, nitriles, sulfoxides, and their mixtures, such as those described in the section of the method (a). Of those, preferred are water-immiscible aliphatic or aromatic hydrocarbons, such as heptane, cyclohexane, toluene, etc.

The amount of the solvent to be used is preferably from 0 to 30 parts by mass relative to 1 part by mass of the organic phosphorus-carboxylic acid, more preferably from 1 to 10 parts by mass.

In case where an acid catalyst is used in the method (b), the acid catalyst usable therein includes mineral acids, such as sulfuric acid, phosphoric acid, etc.; sulfonic acids, such as paratoluenesulfonic acid, methanesulfonic acid, trifluoromethanesulfonic acid, etc.; Lewis acids, such as trifluoroboric acid, tetraisopropoxytitanium, etc.; solid acids such as zeolite, acid resins, etc.; and their mixed acids. Of those, preferred are sulfonic acids such as paratoluenesulfonic acid, methanesulfonic acid, trifluoromethanesulfonic acid, etc.; and Lewis acids such as tetraisopropoxytitanium, etc. The amount of the catalyst to be used is preferably from 0.001 to 5 mols relative to 1 mol of the organic phosphorus-carboxylic acid from the viewpoint of preventing side reaction, more preferably from 0.01 to 1 mol, even more preferably from 0.01 to 0.3 mols.

In case where a dehydrating agent is used, the usable dehydrating agent may be one or more selected from dicyclohexylcarbodiimide, N,N'-carbonyldiimidazole, di-2-pyridyl carbonate, phenyl dichlorophosphate, a mixture of ethyl diethylazodicarboxylate and triphenyl phosphine, etc. The amount of the dehydrating agent to be used is preferably from 0.8 to 10 mols relative to 1 mol of the organic phosphorus-carboxylic acid, more preferably from 0.9 to 5 mols, even more preferably from 1 to 3 mols.

In the reaction of the method (b) where an acid catalyst is used, the lower limit of the reaction temperature is preferably not lower than 0° C., and from the viewpoint of not lowering the reactivity, the reaction temperature is more preferably not lower than 20° C. On the other hand, from the viewpoint of preventing side reaction and production decomposition, the upper limit of the reaction temperature is preferably not higher than 200° C., more preferably not higher than 150° C.

The lower limit of the reaction temperature in the case where a dehydrating agent is used is preferably not lower than $-20°$ C., and from the viewpoint of not lowering the reactivity, the reaction temperature is more preferably not lower than 0° C. On the other hand, from the viewpoint of preventing side reaction and production decomposition, the upper limit of the reaction temperature is preferably not higher than 100° C., more preferably not higher than 50° C.

The reaction time for the method (b) may be varied suitably, depending on the reaction temperature and the reaction scale; however, when the reaction time is too short, then unreacted matters may remain, but on the contrary, when the reaction time is too long, then the reaction product would be decomposed and some side reaction would occur. Therefore, the reaction time is preferably from 0.1 to 24 hours, more preferably from 0.2 to 12 hours.

[Method (c)]

The method (c) comprises reacting an organic phosphorus-carboxylic acid ester with a corresponding hydroxy compound through transesterification in or not in a solvent and in the presence of a catalyst.

In the reaction of the method (c), the amount of the hydroxy compound to be used is preferably from 0.9 to 20 mols relative to 1 mol of the organic phosphorus-carboxylic acid therein, more preferably from 1 to 15 mols, even more preferably from 1 to 8 mols.

The hydroxy compound to be used in the method (c) includes those described in the section of the method (a).

The reaction of the method (c) may advance in the absence of a solvent, for which, however, a solvent inert to the reaction may be used. The solvent to be used includes aliphatic hydrocarbons, halogenohydrocarbons, aromatic hydrocarbons, halogenoaromatic hydrocarbons, ethers, nitriles, sulfoxides, and their mixtures, such as those described in the section of the method (a). Of those, preferred are water-immiscible aliphatic or aromatic hydrocarbons, such as heptane, cyclohexane, toluene, etc.

The amount of the solvent to be used is preferably from 0 to 30 parts by mass relative to 1 part by mass of the organic phosphorus-carboxylic acid ester, more preferably from 1 to 10 parts by mass.

The catalyst for use in the method (c) may be any of an acid catalyst or a basic catalyst. The acid catalyst usable therein includes mineral acids, such as sulfuric acid, phosphoric acid, etc.; sulfonic acids, such as paratoluenesulfonic acid, methanesulfonic acid, trifluoromethanesulfonic acid, etc.; Lewis acids, such as trifluoroboric acid, tetramethoxytitanium, tetraisopropoxytitanium, etc.; solid acids, such as zeolite, acid resins, etc.; and their mixed acids. Of those, preferred are Lewis acids, such as tetramethoxytitanium, tetraisopropoxytitanium, etc. The usable base includes alkali metal carbonates, such as sodium carbonate, potassium carbonate, etc.; alkali metal alcoholates, such as sodium methylate, sodium ethylate, potassium tert-butoxide, etc.; alkali metal hydrides, such as sodium hydride, potassium hydride, etc.; alkali metals, such as sodium, potassium, lithium, etc.; and their mixtures. Of those, preferred are alkali metal carbonates, such as sodium carbonate, potassium carbonate, etc. The amount of the catalyst to be used is preferably from 0.001 to 5 mols relative to 1 mol of the organic phosphorus-carboxylic acid ester, more preferably from 0.005 to 1 mol, even more preferably from 0.01 to 0.3 mols, as capable of preventing side reaction.

In the reaction of the method (c), the lower limit of the reaction temperature is preferably not lower than 0° C., and from the viewpoint of not lowering the reactivity, the reaction temperature is more preferably not lower than 20° C. On the other hand, from the viewpoint of preventing side reaction and production decomposition, the upper limit of the reaction temperature is preferably not higher than 200° C., more preferably not higher than 150° C. The reaction time may be varied suitably, depending on the reaction temperature and the reaction scale; however, when the reaction time is too short, then unreacted matters may remain, but on the contrary, when the reaction time is too long, then the reaction product would be decomposed and some side reaction would occur. Therefore, the reaction time is preferably from 0.1 to 24 hours, more preferably from 0.2 to 15 hours.

EXAMPLES

Synthesis Examples of the organic phosphorus compound for use in the present invention are shown below; however, the present invention is not limited to these Examples.

Synthesis Example 1

Synthesis of 2-propynyl 2-(diethoxyphosphoryl)acetate (synthetic compound 1)

100.0 g (0.51 mol) of 2-(diethoxyphosphoryl)acetic acid, 400 mL of toluene and N,N-dimethylformamide (0.1 g) were stirred at 50° C., and 67.7 g (0.54 mol) of 95% thionyl chloride was dropwise added thereto, taking 20 minutes. Subsequently, this was stirred at 63° C. for 90 minutes, and the solvent was evaporated away to prepare 2-(diethoxyphosphoryl)acetic acid chloride.

The above 2-(diethoxyphosphoryl)acetic acid chloride and 31.4 g (0.56 mol) of propargyl alcohol were dissolved in 100 mL of toluene and cooled to 5° C. 67.1 g (0.66 mol) of triethylamine was dropwise added to the solution at 15° C. or lower, then stirred at room temperature for 90 minutes, and disappearance of the starting materials was confirmed through gas chromatography. The formed salt was filtered and washed with 30 ml of a saturated saline solution. The organic layer was concentrated under reduced pressure, and the resulting residue was purified through silica gel column chromatography (ethyl acetate/hexane=1/1 for elution) to give 111.9 g (yield 93%) of the intended 2-propynyl 2-(diethoxyphosphoryl)acetate. The obtained 2-propynyl 2-(diethoxyphosphoryl)acetate was analyzed through $^1$H-NMR to confirm the structure thereof. The results are shown below.

2-Propynyl 2-(diethoxyphosphoryl)acetate $^1$H-NMR (300 MHz, CDCl$_3$): δ=4.74 (d, J=2.4 Hz, 2H), 4.24-4.13 (m, 4H), 3.02 (d, J=21.7 Hz, 2H), 2.50 (t, J=2.4 Hz, 1H), 1.38-1.33 (m, 6H)

Similarly, 2-(diethoxyphosphoryl)acetic acid chloride was reacted with a corresponding alcohol to give the following compounds.

Synthetic Compound 2

1-Methyl-2-propynyl 2-(diethoxyphosphoryl)acetate $^1$H-NMR (300 MHz, CDCl$_3$): δ=5.51-5.44 (m, 1H), 4.23-4.14 (m, 4H), 2.99 (dd, J=21.5 Hz, 0.5 Hz, 2H), 2.48 (d, J=2.2 Hz, 1H), 1.53 (d, J=6.6 Hz, 3H), 1.36 (t, J=7.1 Hz, 6H)

Synthetic Compound 3

1,1-dimethyl-2-propynyl 2-(diethoxyphosphoryl)acetate $^1$H-NMR (300 MHz, CDCl$_3$): δ=4.23-4.13 (m, 4H), 2.94 (d, J=21.0 Hz, 2H), 2.55 (s, 1H), 1.70 (s, 6H), 1.37-1.32 (m, 6H)

Synthetic Compound 4

2-Butyne-1,4-diyl bis(2-(diethoxyphosphoryl)acetate)

$^1$H-NMR (300 MHz, CDCl$_3$): δ=4.77 (s, 4H), 4.23-4.13 (m, 8H), 3.00 (d, J=21.5 Hz, 4H), 1.38-1.32 (m, 12H)

Synthetic Compound 5

4-Trifluoromethylphenyl 2-(diethoxyphosphoryl)acetate $^1$H-NMR (300 MHz, CDCl$_3$): δ=7.66 (d, J=8.3 Hz, 2H), 7.26 (d, J=8.3 Hz, 2H), 4.26-4.19 (m, 4H), 3.21 (d, J=21.7 Hz, 2H), 1.40-1.36 (m, 6H)

Synthetic Compound 6

2-Cyanoethyl 2-(diethoxyphosphoryl)acetate $^1$H-NMR (300 MHz, CDCl$_3$): δ=4.38-4.33 (m, 2H), 4.25-4.13 (m, 4H), 3.02 (d, J=21.7 Hz, 2H), 2.77-2.72 (m, 2H), 1.38-1.34 (m, 6H)

Synthesis Example 2

Synthesis of 2-(2-(diethoxyphosphoryl)acetoxyl)ethyl methyl oxalate (synthetic compound 7)

2.0 g (13.51 mmol) of 2-hydroxyethylmethyl oxalate and 1.7 g (16.8 mmol) of triethylamine were dissolved in 50 mL of ethyl acetate, and 3.1 g (14.5 mmol) of diethyl (2-chloro-2-oxoethyl)phosphonate was dropwise added thereto at 15° C. or lower, taking 15 minutes. This was stirred at room temperature for 1 hour, and the disappearance of the starting materials was confirmed through gas chromatography. The reaction liquid was washed with water, the organic layer was concentrated under reduced pressure, and the resulting residue was purified through silica gel column chromatography (ethyl acetate for elution) to give 1.8 g (yield 42%) of the intended 2-(2-(diethoxyphosphoryl)acetoxyl)ethyl methyl oxalate.

The obtained 2-(2-(diethoxyphosphoryl)acetoxyl)ethyl methyl oxalate was analyzed through $^1$H-NMR to confirm the structure thereof. The results are shown below.

2-(2-(Diethoxyphosphoryl)acetoxyl)ethyl methyl oxalate $^1$H-NMR (300 MHz, CDCl$_3$): δ=4.53-4.42 (m, 4H), 4.23-4.12 (m, 4H), 3.92 (s, 3H), 3.00 (d, J=21.5 Hz, 2H), 1.37-1.32 (m, 6H)

Synthesis Example 3

Synthesis of 2-propynyl 2-(diethoxyphosphoryl)-2-fluoroacetate (synthetic compound 8)

45.31 g (826 mmol) of propargyl alcohol and 0.94 g (4.1 mmol of tetraethyl titanate were added to 10.00 g (41.3 mmol) of ethyl 2-(diethoxyphosphoryl)-2-fluoroacetate, and heated under reflux at 100° C. for 10 hours. Subsequently, ethanol and propargyl alcohol were evaporated away under reduced pressure at a temperature falling within a range of from 70° C. to 100° C., taking 10 hours, and then the residue was cooled down to room temperature. 0.18 g of water was added to the reaction liquid, the formed precipitate was filtered away, and the filtrate was purified through silica gel column chromatography (ethyl acetate/hexane=1/1 for elution) to give 8.96 g (yield 86%) of the intended 2-propynyl 2-(diethoxyphosphoryl)-2-fluoroacetate. The obtained 2-propynyl 2-(diethoxyphosphoryl)-2-fluoroacetate was analyzed through $^1$H-NMR to confirm the structure thereof. The results are shown below.

2-Propynyl 2-(diethoxyphosphoryl)-2-fluoroacetate $^1$H-NMR (400 MHz, CDCl$_3$): δ=5.28 (dd, J=46.8 Hz, 12.8 Hz, 1H), 4.87 (d, J=2.5 Hz, 2H), 4.33-4.22 (m, 4H), 2.57 (t, J=2.5 Hz, 1H), 1.41-1.32 (m, 6H)

Examples of electrolytic solutions using the organic phosphorus compound of the present invention are shown below; however, the present invention is not limited to these Examples.

Examples 1 to 31, Comparative Examples 1 and 2

Production of Lithium Ion Secondary Battery

94% by mass of LiCo$_{1/3}$Ni$_{1/3}$Mn$_{1/3}$O$_2$ (positive electrode active material, the pH of the supernatant prepared by dispersing 10 g of the positive electrode active material in 100 ml of distilled water was 11.1) and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.5 g/cm$^3$. The electrode sheet was analyzed through X-ray diffractometry, and the ratio of the peak intensity I(110) of the (110) plane of the graphite crystal to the peak intensity I(004) of the (004) plane thereof [I(110)/I(004)] was 0.1. The positive electrode sheet, a porous polyethylene film separator and the negative electrode sheet were laminated in that order, and the nonaqueous electrolytic solution having the composition shown in Table 1 and Table 2 was added thereto to construct a 2032 coin-type battery.

Evaluation of High-Temperature Cycle Properties

In a thermostatic chamber kept at 60° C., the battery produced according to the above-mentioned method was charged up to a final voltage of 4.3 V for 3 hours with a constant current of 1 C and a constant voltage, and then discharged under a constant current of 1 C to a discharging voltage of 3.0 V. This is one cycle. The cycle was repeated up to 100 cycles. According to the equation mentioned below, the capacity retention rate after cycles was calculated.

Capacity Retention Rate (%)=(discharge capacity after 100 cycles/discharge capacity after 1 cycle)×100.

The condition in producing the batteries and the battery characteristics are shown in Table 1 to Table 3.

TABLE 1

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 1 | 1.2M LiPF6 EC/DMC/MEC (30/50/20) | 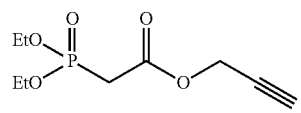 | 1 | 73 |

TABLE 1-continued

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 2 | 1.2M LiPF6 + 0.05M LiBF4 EC/VC/DMC/MEC (29/1/50/20) | 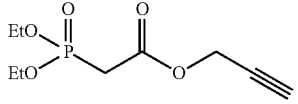 | 0.1 | 70 |
| Example 3 | 1.2M LiPF6 + 0.05M LiBF4 EC/VC/DMC/MEC (29/1/50/20) | 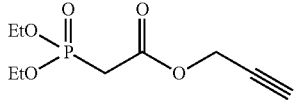 | 1 | 80 |
| Example 4 | 1.2M LiPF6 + 0.05M LiBF4 EC/VC/DMC/MEC (29/1/50/20) | 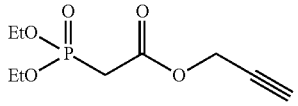 | 3 | 78 |
| Example 5 | 1.2M LiPF6 + 0.05M LiBF4 EC/VC/DMC/MEC (29/1/50/20) | 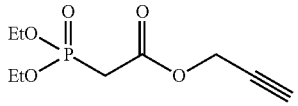 | 7 | 75 |
| Example 6 | 1.2M LiPF6 + 0.05M LiBF4 EC/FEC/VC/DMC/MEC (24/5/1/50/20) | 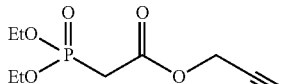 | 1 | 86 |
| Example 7 | 1.2M LiPF6 + 0.05M LiN(SO2F)2 EC/VC/DMC/MEC (29/1/50/20) | 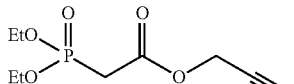 | 1 | 82 |
| Example 8 | 1.2M LiPF6 + 0.05M LiBF4 EC/VC/DMC/MEC (29/1/50/20) | 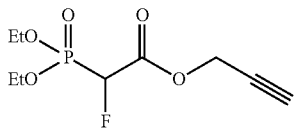 [SMILES: C#CCOC(=O)C(F)P(=O)(OCC)OCC] | 1 | 79 |
| Example 9 | 1.2M LiPF6 + 0.05M LiBF4 EC/VC/DMC/MEC (29/1/50/20) | 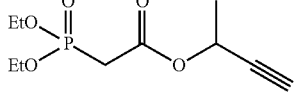 | 1 | 78 |
| Example 10 | 1.2M LiPF6 + 0.05M LiBF4 EC/VC/DMC/MEC (29/1/50/20) | 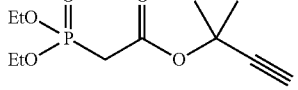 | 1 | 77 |
| Example 11 | 1.2M LiPF6 + 0.05M LiBF4 EC/VC/DMC/MEC (29/1/50/20) | 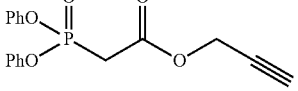 | 1 | 78 |
| Example 12 | 1.2M LiPF6 + 0.05M LiBF4 EC/VC/DMC/MEC (29/1/50/20) | 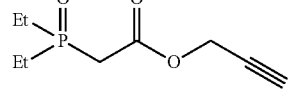 | 1 | 75 |
| Example 13 | 1.2M LiPF6 + 0.05M LiBF4 EC/VC/DMC/MEC (29/1/50/20) | 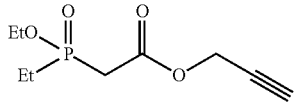 | 1 | 74 |

TABLE 1-continued

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 14 | 1.2M LiPF6 + 0.05M LiBF4 EC/VC/DMC/MEC (29/1/50/20) | 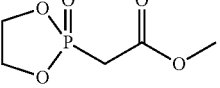 | 1 | 74 |
| Example 15 | 1.2M LiPF6 + 0.05M LiBF4 EC/VC/DMC/MEC (29/1/50/20) | 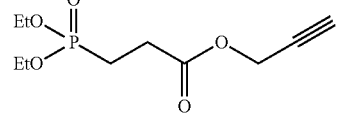 | 1 | 74 |
| Example 16 | 1.2M LiPF6 + 0.05M LiBF4 EC/VC/DMC/MEC (29/1/50/20) | 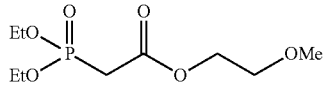 [SMILES: CCOP(=O)(CC(=O)OCCOC)OCC] | 1 | 76 |
| Example 17 | 1.2M LiPF6 + 0.05M LiBF4 EC/VC/DMC/MEC (29/1/50/20) | 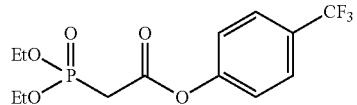 [SMILES: CCOP(=O)(CC(=O)Oc1ccc(C(F)(F)F)cc1)OCC] | 1 | 77 |
| Example 18 | 1.2M LiPF6 + 0.05M LiBF4 EC/VC/DMC/MEC (29/1/50/20) | 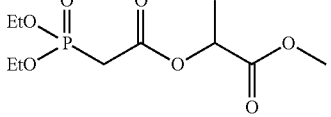 | 1 | 78 |
| Example 19 | 1.2M LiPF6 + 0.05M LiBF4 EC/VC/DMC/MEC (29/1/50/20) | 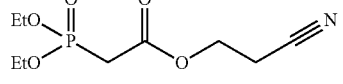 | 1 | 77 |
| Example 20 | 1.2M LiPF6 + 0.05M LiBF4 EC/VC/DMC/MEC (29/1/50/20) | 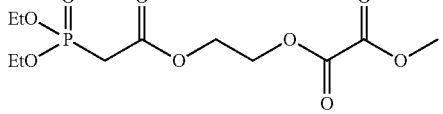 | 1 | 77 |
| Example 21 | 1.2M LiPF6 + 0.05M LiBF4 EC/VC/DMC/MEC (29/1/50/20) | 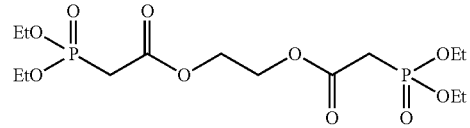 [SMILES: CCOP(=O)(CC(=O)OCCOC(=O)CP(=O)(OCC)OCC)OCC] | 1 | 82 |
| Example 22 | 1.2M LiPF6 + 0.05M LiBF4 EC/VC/DMC/MEC (29/1/50/20) | 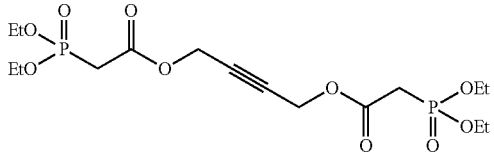 [SMILES: CCOP(=O)(CC(=O)OCC#CCOC(=O)CP(=O)(OCC)OCC)OCC] | 1 | 83 |
| Comparative Example 1 | 1.2M LiPF6 + 0.05M LiBF4 EC/VC/DMC/MEC (29/1/50/20) | none | — | 63 |
| Comparative Example 2 | 1.2M LiPF6 + 0.05M LiBF4 EC/VC/DMC/MEC (29/1/50/20) | 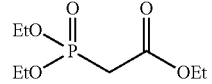 | 1 | 67 |

TABLE 2

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Other Additive | Amount of Other Additive Added (content (wt %) in nonaqueous electrolytic solution) | Discharge Capacity Retention Rate (%) after 100 cycles at 60° C. |
|---|---|---|---|---|---|---|
| Example 23 | 1.2M LiPF6 + 0.05M LiBF4 EC/VC/DMC/MEC (29/1/50/20) | EtO-P(=O)(OEt)-CH2-C(=O)-O-CH2-C≡CH | 1 | adiponitrile | 0.3 | 87 |
| Example 24 | 1.2M LiPF6 + 0.05M LiBF4 EC/VC/DMC/MEC (29/1/50/20) | EtO-P(=O)(OEt)-CH2-C(=O)-O-CH2-C≡CH | 1 | 1,3-propanesultone | 2 | 88 |
| Example 25 | 1.2M LiPF6 + 0.05M LiBF4 EC/VC/DMC/MEC (29/1/50/20) | EtO-P(=O)(OEt)-CH2-C(=O)-O-CH2-C≡CH | 1 | di(2-propynyl) oxalate | 0.5 | 89 |
| Example 26 | 1.2M LiPF6 + 0.05M LiBF4 EC/VC/DMC/MEC (29/1/50/20) | EtO-P(=O)(OEt)-CH2-C(=O)-O-CH2-C≡CH | 1 | 2-butyne-1,4-diyl dimethane-sulfonate | 0.5 | 89 |
| Example 27 | 1.2M LiPF6 + 0.05M LiBF4 EC/VC/DMC/MEC (29/1/50/20) | EtO-P(=O)(OEt)-CH2-C(=O)-O-CH2-C≡CH | 1 | ethyl diethyl-phosphono-acetate | 0.1 | 87 |
| Example 28 | 1.2M LiPF6 + 0.05M LiPF2(C2O4)2 EC/VC/DMC/MEC (29/1/50/20) | EtO-P(=O)(OEt)-CH2-C(=O)-O-CH2-C≡CH | 1 | none | — | 87 |
| Comparative Example 1 | 1.2M LiPF6 + 0.05M LiBF4 EC/VC/DMC/MEC (29/1/50/20) | none | — | none | — | 63 |
| Comparative Example 2 | 1.2M LiPF6 + 0.05M LiBF4 EC/VC/DMC/MEC (29/1/50/20) | EtO-P(=O)(OEt)-CH2-C(=O)-OEt | 1 | none | — | 67 |

TABLE 3

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 29 | 1.2M LiPF6 + 0.05M LiBF4 EC/VC/DMC/MEC (29/1/50/20) | EtO-P(=O)(OEt)-CH2-O-C(=O)-C(=O)-O-CH3 | 1 | 74 |
| Example 30 | 1.2M LiPF6 + 0.05M LiBF4 EC/VC/DMC/MEC (29/1/50/20) | EtO-P(=O)(OEt)-CH2-O-C(=O)-CH3 | 1 | 72 |

TABLE 3-continued

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 31 | 1.2M LiPF6 + 0.05M LiBF4 EC/VC/DMC/MEC (29/1/50/20) | (EtO)$_2$P(O)CH$_2$OC(O)C(O)OCH$_2$P(O)(OEt)$_2$ | 1 | 75 |
| Comparative Example 1 | 1.2M LiPF6 + 0.05M LiBF4 EC/VC/DMC/MEC (29/1/50/20) | none | — | 63 |
| Comparative Example 2 | 1.2M LiPF6 + 0.05M LiBF4 EC/VC/DMC/MEC (29/1/50/20) | (EtO)$_2$P(O)CH$_2$C(O)OEt | 1 | 67 |

Example 32, Comparative Example 3

A negative electrode sheet was produced, using silicon (elementary substance) (negative electrode active material) in place of the negative electrode active material used in Example 3 and Comparative Example 1. Precisely, 80% by mass of silicon (elementary substance) and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin-type batteries were produced and evaluated in the same manner as in Example 1 and Comparative Example 1, except that the negative electrode sheet produced herein was used. The results are shown in Table 4.

Example 33, Comparative Example 4

A positive electrode sheet was produced by changing the positive electrode active material used in Example 3 and Comparative Example 1 to LiFePO$_4$ (positive electrode active material) coated with amorphous carbon. Concretely, 90% by mass of LiFePO$_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin-type batteries were produced and evaluated in the same manner as in Example 1 and Comparative Example 1, except that the positive electrode sheet thus produced herein was used and that, in battery evaluation, the final charging voltage was changed to 3.6 V and the final discharging voltage was changed to 2.0 V. The results are shown in Table 5.

TABLE 4

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 32 | 1.2M LiPF6 + 0.05M LiBF4 EC/VC/DMC/MEC (29/1/50/20) | (EtO)$_2$P(O)CH$_2$C(O)OCH$_2$C≡CH | 1 | 68 |
| Comparative Example 3 | 1.2M LiPF6 + 0.05M LiBF4 EC/VC/DMC/MEC (29/1/50/20) | (EtO)$_2$P(O)CH$_2$C(O)OEt | 1 | 55 |

TABLE 5

| | Composition of Electrolyte Salt Composition of Nonaqueous Electrolytic Solution (ratio by volume of solvents) | Organic Phosphorus Compound | Amount of Organic Phosphorus Compound Added (content (wt %) in nonaqueous electrolytic solution) | Discharge Capacity Retention Rate (%) after 100 cycles at 60° C. |
|---|---|---|---|---|
| Example 33 | 1.2M LiPF6 + 0.05M LiBF4 EC/VC/DMC/MEC (29/1/50/20) | EtO–P(=O)(OEt)–CH2–C(=O)–O–CH2–C≡CH | 1 | 82 |
| Comparative Example 4 | 1.2M LiPF6 + 0.05M LiBF4 EC/VC/DMC/MEC (29/1/50/20) | EtO–P(=O)(OEt)–CH2–C(=O)–OEt | 1 | 60 |

The lithium secondary batteries of Examples 1 to 31 were all remarkably bettered in point of the cycle properties thereof at high temperatures and especially at high charging voltage, as compared with the lithium secondary battery of Comparative Example 1 to which the organic phosphorus compound of the present invention was not added to the nonaqueous electrolytic solution, and that of Comparative Example 2 to which triethylphosphonoacetate described in PTL 1 was added. From the above, it has been clarified that the advantageous effect of the present invention is peculiar to the nonaqueous electrolytic solution of an electrolyte salt dissolved in a nonaqueous solvent that contains the specific organic phosphorus compound of the present invention.

In addition, from comparison of Example 32 with Comparative Example 3, and from comparison of Example 33 with Comparative Example 4, the same advantageous effect is seen in the case where silicon (elementary substance) was used as the negative electrode and in the case where a lithium-containing olivine-type iron phosphate was used as the positive electrode. Accordingly, it is obvious that the advantageous effect of the present invention does not depend on any specific positive electrode or negative electrode.

Further, the nonaqueous electrolytic solution of the present invention has an effect of improving the discharge characteristics of lithium primary batteries at high temperatures.

INDUSTRIAL APPLICABILITY

Using the nonaqueous electrolytic solution of the present invention provides energy storage devices excellent in electrochemical characteristics at high temperatures. In particular, when the nonaqueous electrolytic solution is used for energy storage devices to be mounted on hybrid electric vehicles, plug-in hybrid electric vehicles, battery electric vehicles, etc., there can be obtained energy storage devices of which the electrochemical characteristics are hardly worsened at high temperatures.

The invention claimed is:
1. A nonaqueous electrolytic solution, comprising:
an electrolyte salt dissolved in a non-aqueous solvent, and
an organic phosphorus compound of formula (I):

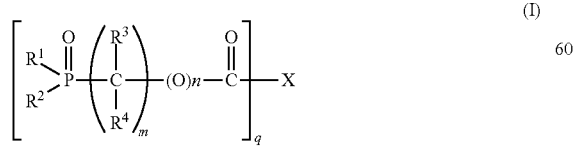

(I)

wherein
$R^1$ and $R^2$ each independently represent an alkyl group comprising from 1 to 6 carbon atoms, a cycloalkyl group comprising from 3 to 6 carbon atoms, an alkenyl group comprising from 2 to 6 carbon atoms, an alkynyl group comprising from 3 to 6 carbon atoms, an alkoxy group comprising from 1 to 6 carbon atoms, a cycloalkoxy group comprising from 3 to 6 carbon atoms, an alkenyloxy group comprising from 2 to 6 carbon atoms, an alkynyloxy group comprising from 3 to 6 carbon atoms, a halogenoalkyl group comprising from 1 to 6 carbon atoms, a halogenoalkoxy group comprising from 1 to 6 carbon atoms, an aryl group comprising from 6 to 12 carbon atoms in which at least one hydrogen atom is optionally substituted with a halogen atom, or an aryloxy group comprising from 6 to 12 carbon atoms in which at least one hydrogen atom is optionally substituted with a halogen atom;
when $R^1$ and $R^2$ each are an alkyl group or an alkoxy group, $R^1$ and $R^2$ optionally bond to form a cyclic structure;
$R^3$ and $R^4$ each independently represent a hydrogen atom, a halogen atom, or an alkyl group comprising from 1 to 4 carbon atoms;
m represents an integer of from 1 to 4;
n represents 0 or 1, q represents 1 or 2, and n, q and X satisfy:
when q is 1 and n is 0, X represents an alkoxy group comprising from 1 to 6 carbon atoms, an alkynyloxy group comprising from 3 to 6 carbon atoms, an alkyloxyalkoxy group comprising from 2 to 6 carbon atoms, an aryloxy group comprising from 6 to 12 carbon atoms in which at least one hydrogen atom is substituted with a halogen atom, —O—L$^1$—OC(=O)—C(=O)—OR$^5$, —O—L$^2$—C(=O)—OR$^5$, or —O—L$^5$—CN, provided that i) when q is 1, n is 0 and X is an alkoxy group comprising from 1 to 6 carbon atoms, $R^1$ and $R^2$ bond to form a cyclic structure, and ii) when q is 1, n is 0 and X is an aryloxy group comprising from 6 to 12 carbon atoms in which at least one hydrogen atom is substituted with a halogen atom, $R^3$ and $R^4$ are both hydrogen atoms;
when q is 1 and n is 1, X represents an alkyl group comprising from 1 to 6 carbon atoms, an alkynyl group comprising from 2 to 6 carbon atoms, an alkoxy group comprising from 1 to 6 carbon atoms, an alkynyloxy group comprising from 3 to 6 carbon atoms, an alkyloxyalkoxy group comprising from 2 to 6 carbon atoms, or —C(=O)—OR$^5$; and
when q is 2, X represents —O—L$^3$—O—, —OC(=O)—C(=O)O— or a single bond;
$R^5$ represents an alkyl group comprising from 1 to 6 carbon atoms;

L¹ and L³ each represent an alkylene group comprising from 2 to 6 carbon atoms, or an alkynylene group comprising from 4 to 8 carbon atoms; and L² and L⁵ each represent an alkylene group comprising from 1 to 6 carbon atoms.

2. The nonaqueous electrolytic solution according to claim 1, wherein a content of the organic phosphorus compound of formula (I) is from 0.001 to 10% by mass.

3. The nonaqueous electrolytic solution according to claim 1, wherein the organic phosphorus compound of formula (I) is at least one selected from the group consisting of 2-propynyl 2-(diethylphosphoryl)acetate, 2-propynyl 2-(ethoxy(ethyl)phosphoryl)acetate, 2-propynyl 2-(dimethoxyphosphoryl)acetate, 2-propynyl 2-(diethoxyphosphoryl)acetate, 2-propynyl 2-(diphenoxyphosphoryl)acetate, 2-propynyl 2-(diethoxyphosphoryl)-2-fluoroacetate, 2-propynyl 3-(diethoxyphosphoryl)propanoate, 1-methyl-2-propynyl 2-(diethoxyphosphoryl)acetate, 1,1-dimethyl-2-propynyl 2-(diethoxyphosphoryl)acetate, 2-methoxyethyl 2-(diethoxyphosphoryl)acetate, 2-trifluoromethylphenyl 2-(diethoxyphosphoryl)acetate, 4-trifluoromethylphenyl 2-(diethoxyphosphoryl)acetate, methyl 2-(2-oxido-1,3,2-dioxaphospholan-2-yl)acetate, 2-(2-(diethoxyphosphoryl)acetoxy)ethyl methyl oxalate, methyl 2-(2-(diethoxyphosphoryl)acetoxy)propanoate, (diethoxyphosphoryl)methyl acetate, (diethoxyphosphoryl)methyl methyl oxalate, ethane-1,2-diyl bis(2-(diethoxyphosphoryl)acetate), 2-butyne-1,4-diyl bis(2-(diethoxyphosphoryl)acetate), bis((dimethoxyphosphoryl)methyl)oxalate, bis((diethoxyphosphoryl)methyl)oxalate, and 2-cyanoethyl 2-(diethoxyphosphoryl)acetate.

4. The nonaqueous electrolytic solution according to claim 1, wherein the nonaqueous solvent comprises a cyclic carbonate and a linear ester.

5. The nonaqueous electrolytic solution according to claim 4, wherein the cyclic carbonate is at least one selected from the group consisting of ethylene carbonate, propylene carbonate, 1,2-butylene carbonate, 2,3-butylene carbonate, 4-fluoro-1,3-dioxolan-2-one, trans or cis-4,5-difluoro-1,3-dioxolan-2-one, vinylene carbonate, and vinylethylene carbonate.

6. The nonaqueous electrolytic solution according to claim 4, wherein the linear ester comprises a methyl group.

7. The nonaqueous electrolytic solution according to claim 1, wherein the electrolyte salt comprises at least one selected from the group consisting of $LiPF_6$, $LiPO_2F_2$, $Li_2PO_3F$, $LiBF_4$, $LiN(SO_2CF_3)_2$, $LiN(SO_2C_2F_5)_2$, $LiN(SO_2F)_2$, lithium difluorobis[oxalate-O,O']phosphate and lithium tetrafluoro[oxalate-O,O']phosphate.

8. The nonaqueous electrolytic solution according to claim 1, further comprising;
at least one compound selected from the group consisting of i) a nitrile, ii) a cyclic or linear S=O group-comprising compound and iii) a triple bond-comprising compound.

9. The nonaqueous electrolytic solution according to claim 8, wherein the at least one compound is a nitrile, which is at least one selected from the group consisting of succinonitrile, glutaronitrile, adiponitrile and pimelonitrile.

10. The nonaqueous electrolytic solution according to claim 8, wherein the at least one compound is a S=O group-comprising compound, which is at least one selected from the group consisting of 1,3-propanesultone, 1,3-butanesultone, 1,4-butanesultone, 2,4-butanesultone, ethylene sulfite and 4-(methylsulfonylmethyl)-1,3,2-dioxathiolane-2-oxide.

11. The nonaqueous electrolytic solution according to claim 8, wherein the at least one compound is a triple bond-comprising compound, which is at least one selected from the group consisting of 2-propynyl methyl carbonate, 2-propynyl methanesulfonate, di(2-propynyl)oxalate, and 2-butyne-1,4-diyl dimethanesulfonate.

12. An energy storage device, comprising:
a positive electrode,
a negative electrode, and
the nonaqueous electrolytic solution according to claim 1.

13. The energy storage device according to claim 12, wherein the positive electrode comprises at least one active material selected from the group consisting of a lithium complex oxide and a lithium-comprising olivine-type phosphate.

14. The energy storage device according to claim 12, wherein the negative electrode comprises at least one active material selected from the group consisting of a lithium metal, a lithium alloy and a carbon material capable of absorbing and releasing lithium.

15. The nonaqueous electrolytic solution according to claim 1, wherein the organic phosphorus compound of formula (I) is included in an amount of from 0.05 to 8% by mass.

16. An organic phosphorus compound of formula (II):

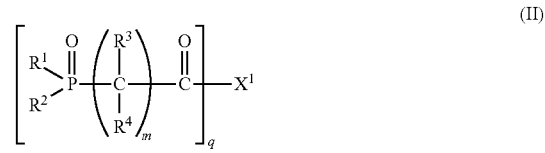

(II)

wherein R¹ and R² each independently represent an alkyl group comprising from 1 to 6 carbon atoms, a cycloalkyl group comprising from 3 to 6 carbon atoms, an alkenyl group comprising from 2 to 6 carbon atoms, an alkynyl group comprising from 3 to 6 carbon atoms, an alkoxy group comprising from 1 to 6 carbon atoms, a cycloalkoxy group comprising from 3 to 6 carbon atoms, an alkenyloxy group comprising from 2 to 6 carbon atoms, an alkynyloxy group comprising from 3 to 6 carbon atoms, a halogenoalkyl group comprising from 1 to 6 carbon atoms, a halogenoalkoxy group comprising from 1 to 6 carbon atoms, an aryl group comprising from 6 to 12 carbon atoms in which at least one hydrogen atom is optionally substituted with a halogen atom, or an aryloxy group comprising from 6 to 12 carbon atoms in which at least one hydrogen atom is optionally substituted with a halogen atom;

when R¹ and R² each are an alkyl group or an alkoxy group, R¹ and R² optionally bond to form a cyclic structure;

R³ and R⁴ each independently represent a hydrogen atom, a halogen atom, or an alkyl group comprising from 1 to 4 carbon atoms;

m represents an integer of from 1 to 4;

q represents 1 or 2;

when q is 1, X¹ represents an alkynyloxy group comprising from 3 to 6 carbon atoms, an aryloxy group comprising from 7 to 12 carbon atoms in which at least one hydrogen atom on the benzene ring is substituted with a trifluoromethyl group, —O-L¹-OC(=O)—C(=O)—OR⁵, —O-L²-C(=O)—OR⁵, or —O-L⁵-CN;

when q is 2, X¹ represents —O-L⁴-O—, or —OC(=O)—C(=O)O—;

R⁵ represents an alkyl group comprising from 1 to 6 carbon atoms;

L¹ represents an alkylene group comprising from 2 to 6 carbon atoms, or an alkynylene group comprising from 4 to 8 carbon atoms;

L² and L⁵ each represent an alkylene group comprising from 1 to 6 carbon atoms; and L⁴ represents an alkynylene group comprising from 4 to 8 carbon atoms.

17. The nonaqueous electrolytic solution according to claim 1, wherein the organic phosphorus compound of formula (I) is included in an amount of from 0.2 to 2% by mass.

18. The nonaqueous electrolytic solution according to claim 1, wherein $R^1$ and $R^2$ each are an alkyl group or an alkoxy group, and $R^1$ and $R^2$ bond to form a cyclic structure.

19. The nonaqueous electrolytic solution according to claim 1, wherein q is 1, n is 0, X is an alkoxy group comprising from 1 to 6 carbon atoms, and $R^1$ and $R^2$ bond to form a cyclic structure.

20. The nonaqueous electrolytic solution according to claim 1, wherein q is 1, n is 0, X is an aryloxy group comprising from 6 to 12 carbon atoms in which at least one hydrogen atom is substituted with a halogen atom, and $R^3$ and $R^4$ are both hydrogen atoms.

\* \* \* \* \*